United States Patent
Shimbo et al.

(10) Patent No.: US 8,755,046 B2
(45) Date of Patent: Jun. 17, 2014

(54) SPECTROMETER, AND IMAGE EVALUATING UNIT AND IMAGE FORMING DEVICE INCORPORATING THE SAME

(71) Applicants: Kohei Shimbo, Kanagawa (JP); Naohiro Kamijo, Kanagawa (JP); Yoichi Kubota, Tokyo (JP); Manabu Seo, Kanagawa (JP)

(72) Inventors: Kohei Shimbo, Kanagawa (JP); Naohiro Kamijo, Kanagawa (JP); Yoichi Kubota, Tokyo (JP); Manabu Seo, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 13/788,058

(22) Filed: Mar. 7, 2013

(65) Prior Publication Data
US 2013/0235249 A1    Sep. 12, 2013

(30) Foreign Application Priority Data
Mar. 9, 2012  (JP) ................................. 2012-052462

(51) Int. Cl.
*G01J 3/28* (2006.01)
(52) U.S. Cl.
USPC .......................................................... 356/328
(58) Field of Classification Search
USPC ......................................... 356/326, 328, 334
See application file for complete search history.

(56) References Cited

U.S. PATENT DOCUMENTS

| | | | |
|---|---|---|---|
| 5,731,874 A * | 3/1998 | Maluf ............................. | 356/326 |
| 7,671,984 B2 * | 3/2010 | Schebesta et al. ............. | 356/326 |
| 2008/0291445 A1 | 11/2008 | Iwane | |
| 2011/0063615 A1 | 3/2011 | Shimbo et al. | |
| 2011/0106472 A1 | 5/2011 | Seo et al. | |
| 2011/0222056 A1 | 9/2011 | Seo et al. | |
| 2011/0299104 A1 | 12/2011 | Seo et al. | |
| 2011/0317149 A1 | 12/2011 | Shimbo et al. | |

FOREIGN PATENT DOCUMENTS

| EP | 1344193 B1 | 7/2007 |
|---|---|---|
| JP | 2008-256594 | 10/2008 |

OTHER PUBLICATIONS

U.S. Appl. No. 13/559,982, filed Jul. 27, 2012, Kohei Shimbo, et al.
U.S. Appl. No. 13/741,513, filed Jan. 15, 2013, Yoichi Kubota, et al.
U.S. Appl. No. 13/737,157, filed Jan. 9, 2013, Kohei Shimbo, et al.
Miyake, Y., "Analysis and Evaluation of Digital Color Images," University of Tokyo Press, vol. 10, pp. 154-157, Feb. 25, 2000. (Partial English translation).

* cited by examiner

*Primary Examiner* — Tarifur Chowdhury
*Assistant Examiner* — Abdullahi Nur
(74) *Attorney, Agent, or Firm* — Harness, Dickey & Pierce, P.L.C.

(57) ABSTRACT

A spectrometer includes a light source to project a light beam to a target object, a spectral element to disperse the light beam reflected by the target object and including a diffraction element to diffract the light beam, and a light receiving element to receive, at pixels, light beams with different spectral characteristics from each other dispersed by the spectral element, wherein the diffraction element and the light receiving element are integrally formed.

9 Claims, 17 Drawing Sheets

DIRECTION OF UNEVENNESS

SPECTROMETER, AND IMAGE EVALUATING UNIT AND IMAGE FORMING DEVICE INCORPORATING THE SAME

CROSS REFERENCE TO RELATED APPLICATION

The present application is based on and claims priority from Japanese Patent Application No. 2012-52462, filed on Mar. 9, 2012, the disclosure of which is hereby incorporated by reference in its entirety.

BACKGROUND OF THE INVENTION

Field of the Invention

The present invention relates to a spectrometer to measure wavelength spectrum, and an image evaluating unit and an image forming device incorporating the same.

Japanese Patent Application Publication No. 2008-256594, for example, discloses a spectrometer which guides a reflected beam by a target object to a light receiving element via a first lens array, a diaphragm with apertures, a second lens array, a diffraction grating, and a third lens array to measure a wavelength spectrum of the reflected beam.

Such a spectrometer faces a problem that the incidence position of a diffracted image formed by the diffraction grating on the light receiving element is shifted over time or due to oscillation or temperature change. Because of this, it cannot accurately measure a wavelengths spectrum of reflected beam by a target object stably.

SUMMARY OF THE INVENTION

The present invention aims to provide a spectrometer configured to be able to accurately, stably measure the wavelength spectrum of reflected beam by a target object.

According to one aspect of the present invention, a spectrometer includes a light source to project a light beam to a target object, a spectral element to disperse the light beam reflected by the target object and including a diffraction element to diffract the light beam, and a light receiving element to receive, at pixels, light beams with different spectral characteristics from each other dispersed by the spectral element, wherein the diffraction element and the light receiving element are integrally formed.

BRIEF DESCRIPTION OF THE DRAWINGS

Features, embodiments, and advantages of the present invention will become apparent from the following detailed description with reference to the accompanying drawings.

DETAILED DESCRIPTION OF PREFERRED EMBODIMENTS

Hereinafter, one embodiment of the present invention will be described in detail with reference to FIG. 1 to FIG. 17. Wherever possible, the same reference numbers will be used throughout the drawings to refer to the same or like parts.

First Embodiment

Figure 1:
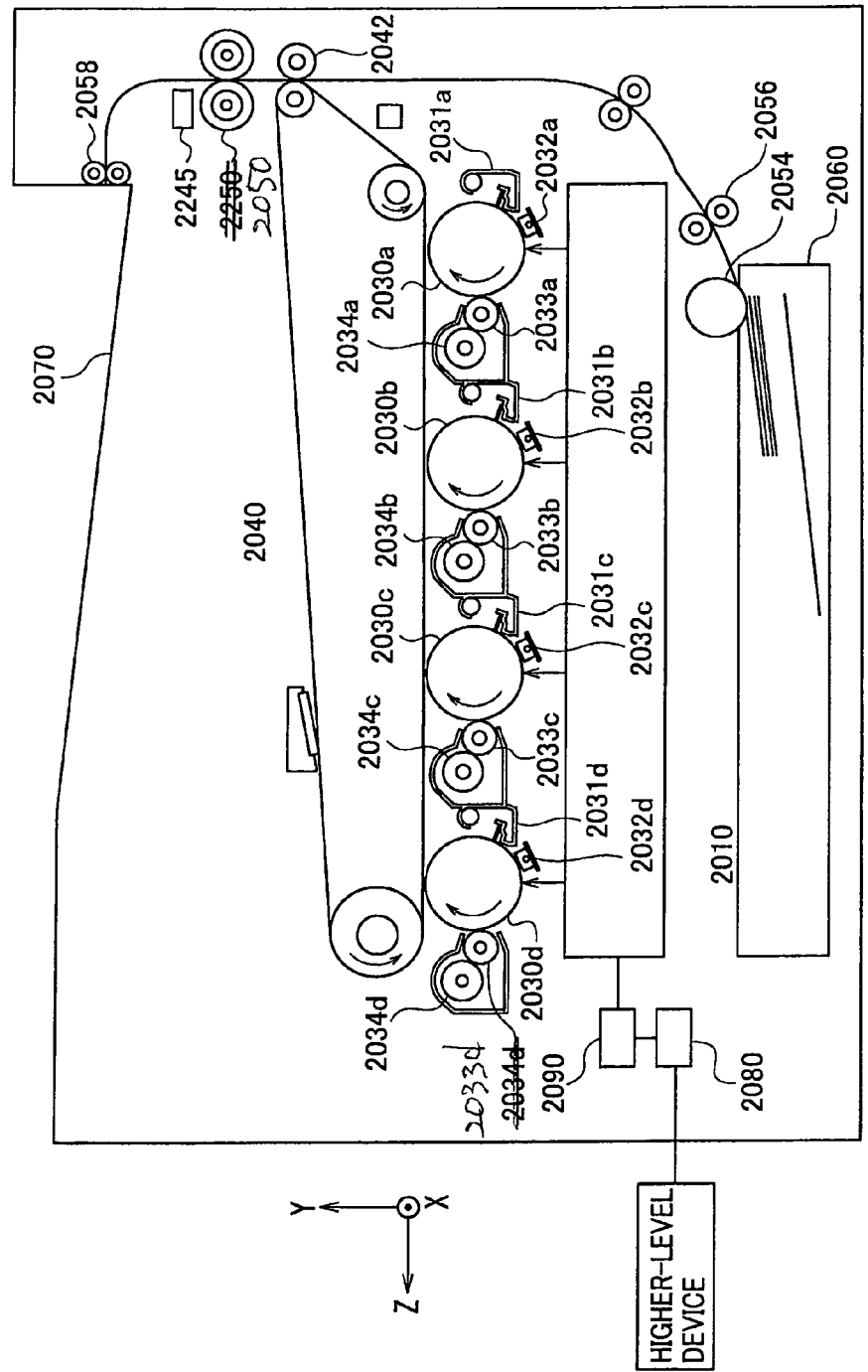
FIG. 1 schematically shows the structure of an image forming device according to a first embodiment of the present invention by way of example.

FIG. 1 schematically shows the structure of an image forming device 2000 according to one embodiment by way of example. The image forming device 2000 is a tandem type, full color image forming device and includes an optical scanner 2010, four photoreceptor drums 2030a to 2030d, four cleaning units 2031a to 2031d, four charging units 2032a to 2032d, four develop rollers 2033a to 2033d, four toner cartridges 2034a to 2034d, a transfer belt 2040, a transfer roller 2042, a fuser unit 2050, a feed roller 2054, a resist roller pair 2056, a discharge roller 2058, a paper tray 2060, a discharge tray 2070, a communication controller 2080, an image quality detector 2245, a not-shown hygrothermal sensor, and a controller 2090 to control these elements.

Note that herein, a longitudinal direction of the photoreceptor drums is defined to be X axis and a direction in which the photoreceptor drums are arranged is defined to be Z axis in an XYZ three-dimensional orthogonal coordinate system.

The communication controller 2080 controls a bidirectional communication with a higher-level device such as a personal computer via a network.

The controller 2090 includes a CPU, an ROM in which programs decodable by the CPU and various kinds of data used in the programs are stored, an RAM as a work memory, and an AD converter. It receives multi-color (black, cyan, magenta, yellow) image data from the higher-level device via the communication controller 2080 and transmits them to the optical scanner 2010.

The hygrothermal sensor detects the temperature and humidity of inside the image forming device 2000 and transmits them to the controller 2090.

The photoreceptor drum 2030a, charging unit 2032a, develop roller 2033a, toner cartridge 2034a, and cleaning unit 2031a constitute a station K to form black images.

The photoreceptor drum 2030b, charging unit 2032b, develop roller 2033b, toner cartridge 2034b, and cleaning unit 2031b constitute a station C to form cyan images.

The photoreceptor drum 2030c, charging unit 2032c, develop roller 2033c, toner cartridge 2034c, and cleaning unit 2031c constitute a station M to form magenta images.

The photoreceptor drum 2030d, charging unit 2032d, develop roller 2033d, toner cartridge 2034d, and cleaning unit 2031d constitute a station Y to form yellow images.

A photosensitive layer is formed on the surface of each photoreceptor drum and scanned with a light beam. Each photoreceptor drum is rotated by a not-shown rotary mechanism in a direction of the arrows in FIG. 1.

The charging units evenly charge the surfaces of the respective photoreceptor drums.

The optical scanner 2010 projects light beams modulated for the four colors to the respective photoreceptor drums according to the multi-color image data from the controller 2090. Charges disappear from the portions of the photoreceptor drum surfaces irradiated with the light beams, forming latent images thereon in accordance with the image data. The latent images are moved to the develop units along with the rotation of the photoreceptor drums.

The toner cartridges 2034a to 2034d contain black, cyan, magenta, yellow toners to supply them to the develop roller 2033a to 2033d, respectively.

The develop rollers are evenly coated with the toners from the corresponding toner cartridges. They function to visualize the latent images by attaching the toners on the surfaces of the photoreceptor drums, to form toner images. The toner images are moved to the transfer belt 2040 along with the rotation of the photoreceptor drums.

The four color toner images are transferred and superimposed in order on the transfer belt 2040 at certain timing to generate a color image.

The paper tray 2060 contains sheets of paper. The feed roller 2054 near the paper tray 2060 extracts the sheets of paper one by one from the paper tray 2060 to the resist roller pair 2056. The resist roller pair 2056 transmits them to a gap between the transfer belt 2040 and transfer roller 2042 at a certain timing. Thereby, the color image is transferred onto the sheets of paper from the transfer belt 2040, and the sheets of paper are then sent to the fuser unit 2050.

The fuser unit 2050 applies heat and pressure to them and fuses the toner thereon. Then, the sheets of paper are sent to the discharge tray 2070 via the discharge roller 2058 and accumulated.

The cleaning units remove remaining toners from the surfaces of the respective photoreceptor drums. Then, the photoreceptor drums are returned to the positions opposing the respective charging units.

The image quality detector 2245 is disposed in the vicinity of a paper carrier path after the fuser unit 2050 to detect the quality of an image on the paper. Results of the detection are transmitted to the controller 2090.

Figure 2:
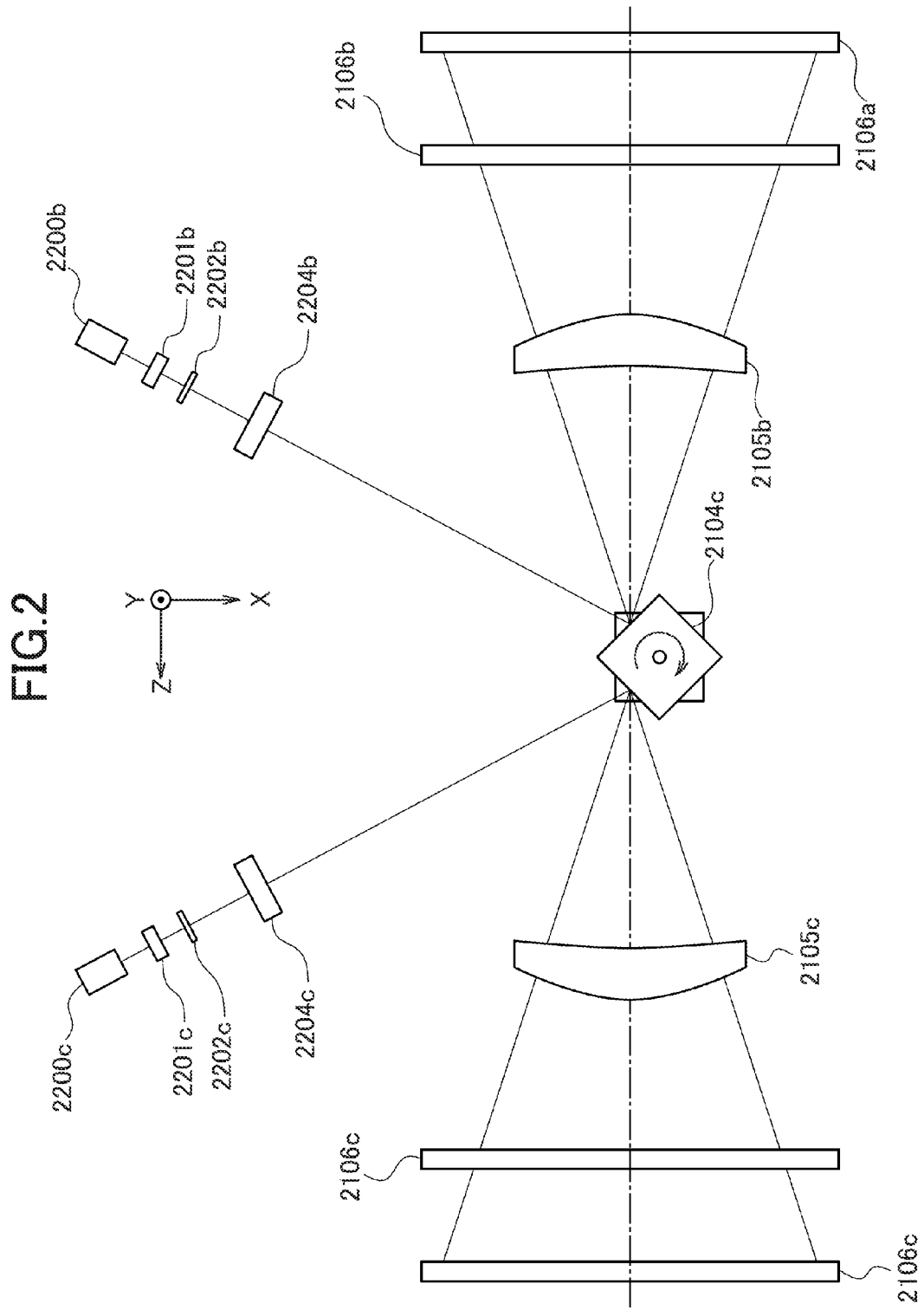
FIG. 2 shows an optical scanner of the imaging forming device in FIG. 1.
Figure 3A:
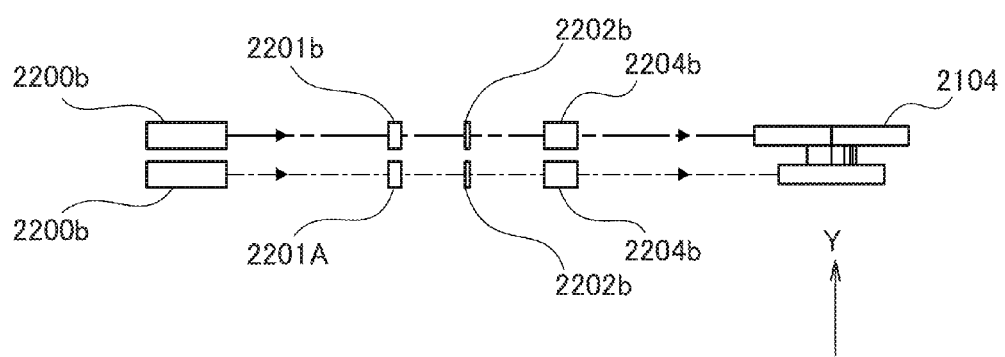
FIGS. 3A, 3B show the optical scanner in FIG. 2.
Figure 3B:
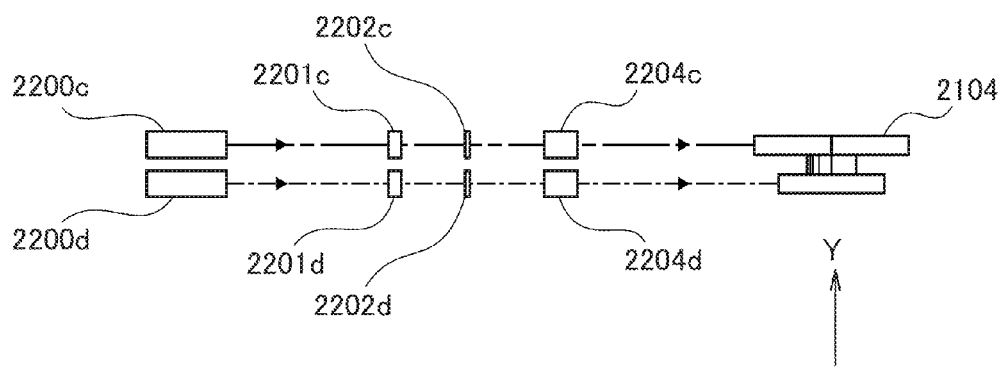
Figure 4:
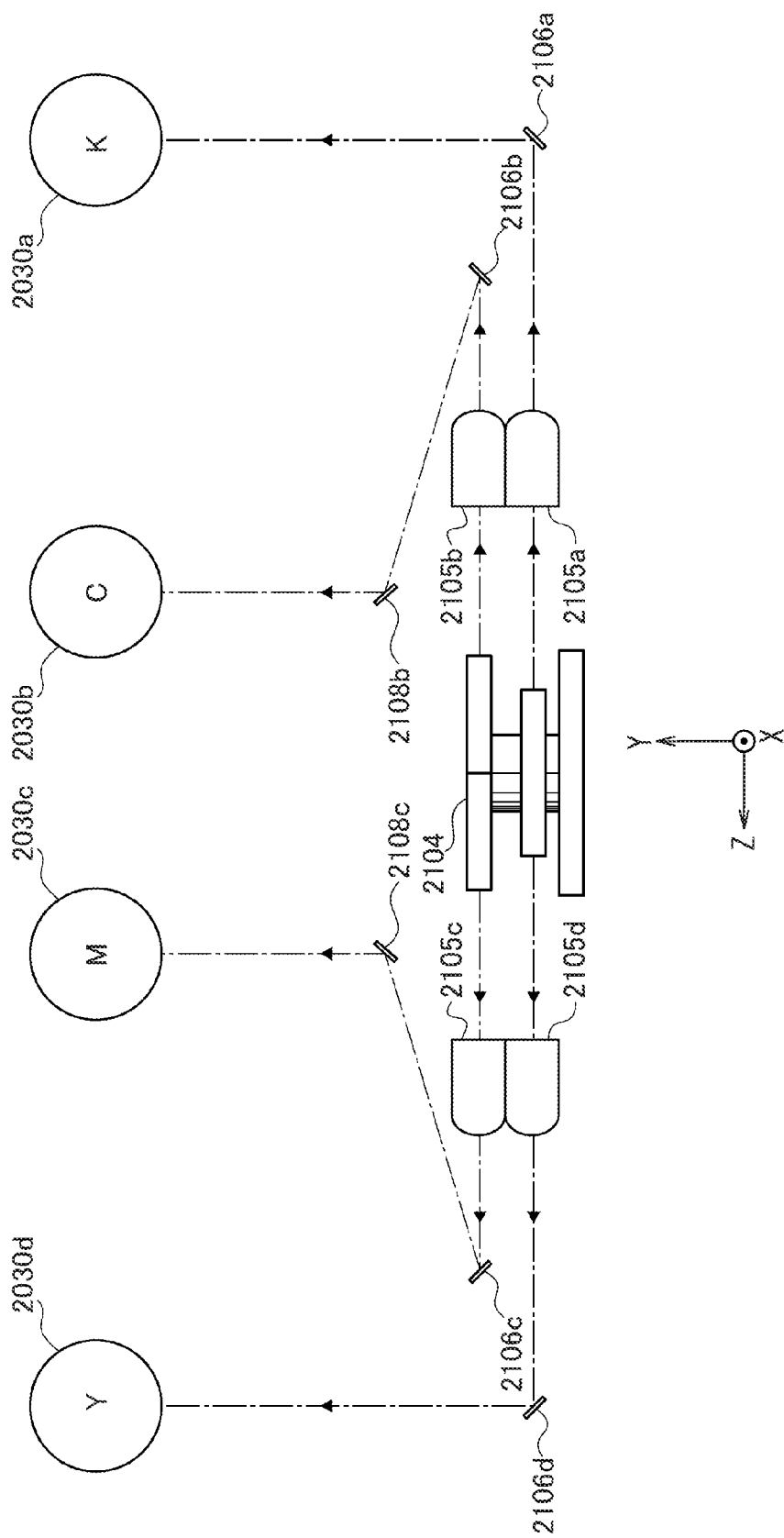
FIG. 4 shows the optical scanner in FIG. 2.

Next, the structure of the optical scanner 2010 is described. Referring to FIG. 2 to FIG. 4, by way of example, the optical scanner 2010 includes four light sources 2200a to 2200d, four coupling lenses 2201a to 2201d, four optical plates 2202a to 2202d, four cylindrical lenses 2204a to 2204d, an optical deflector 2104, four scan lenses 2105a to 2105d, six returning mirrors 2106a to 2106d, 2108b to 2108c, and a not-shown scan controller.

The light source 2200a, coupling lens 2201a, optical plate 2202a, cylindrical lens 2204a, scan lens 2105a and returning mirror 2106a function to form a latent image on the photoreceptor drum 2030a.

The light source 2200b, coupling lens 2201b, optical plates 2202b, cylindrical lens 2204b, scan lens 2105b and returning mirror 2106b function to form a latent image on the photoreceptor drum 2030b.

The light source 2200c, coupling lens 2201c, optical plate 2202c, cylindrical lens 2204c, scan lens 2105c and returning mirror 2106c function to form a latent image on the photoreceptor drum 2030c.

The light source 2200d, coupling lens 2201d, optical plate 2202d, cylindrical lens 2204d, scan lens 2105d and returning mirror 2106d function to form a latent image on the photoreceptor drum 2030d.

The coupling lenses are placed on the paths of light beams from the respective light sources to convert them to parallel beams. The optical plates each include apertures to adjust the shapes of the beams from the coupling lenses. The cylindrical lenses image the light beams having passed through the apertures of the optical plates near the reflective surface of the optical deflector 2104 along Y axis.

The optical deflector 2104 has two-stage polygon mirrors each with four deflection surfaces. A lower-stage polygon mirror deflects the light beams from the cylindrical lenses 2204a and 2204d while an upper-stage polygon mirror deflects the light beams from the cylindrical lenses 2204b and 2204c. The two-stage polygon mirrors are rotated with a phase shift by 45 degrees from each other and scan the light beams alternatively.

The photoreceptor drum 2030a is irradiated with the light beam deflected by the optical reflector 2104 from the cylindrical lens 2204a via the scan lens 2105a and returning mirror 2106a, forming optical spots thereon. The optical spots are moved along the length of the photoreceptor drum 2030a by the rotation of the optical deflector 2104.

Likewise, the photoreceptor drum 2030b is irradiated with the light beam by the optical reflector 2104 from the cylindrical lens 2204b via the scan lens 2105b and two returning mirrors 2106b, 2108b, forming optical spots thereon. The optical spots are moved along the length of the photoreceptor drum 2030b by the rotation of the optical deflector 2104.

The photoreceptor drum 2030c is irradiated with the light beam by the optical reflector 2104 from the cylindrical lens 2204c via the scan lens 2105c and two returning mirror 2106c, 2108c, forming optical spots thereon. The optical spots are moved along the length of the photoreceptor drum 2030c by the rotation of the optical deflector 2104.

The photoreceptor drum 2030d is irradiated with the light beam by the optical reflector 2104 from the cylindrical lens 2204d via the scan lens 2105d and returning mirror 2106d, forming optical spots thereon. The optical spots are moved along the length of the photoreceptor drum 2030d by the rotation of the optical deflector 2104.

The direction in which the optical spots are moved on the photoreceptor drums is a main scan direction while the rotary direction of the photoreceptor drums is a sub scan direction.

The optical system placed on the optical path between the optical deflector 2104 and each photoreceptor drum is referred to as scan optical system.

Figure 5:
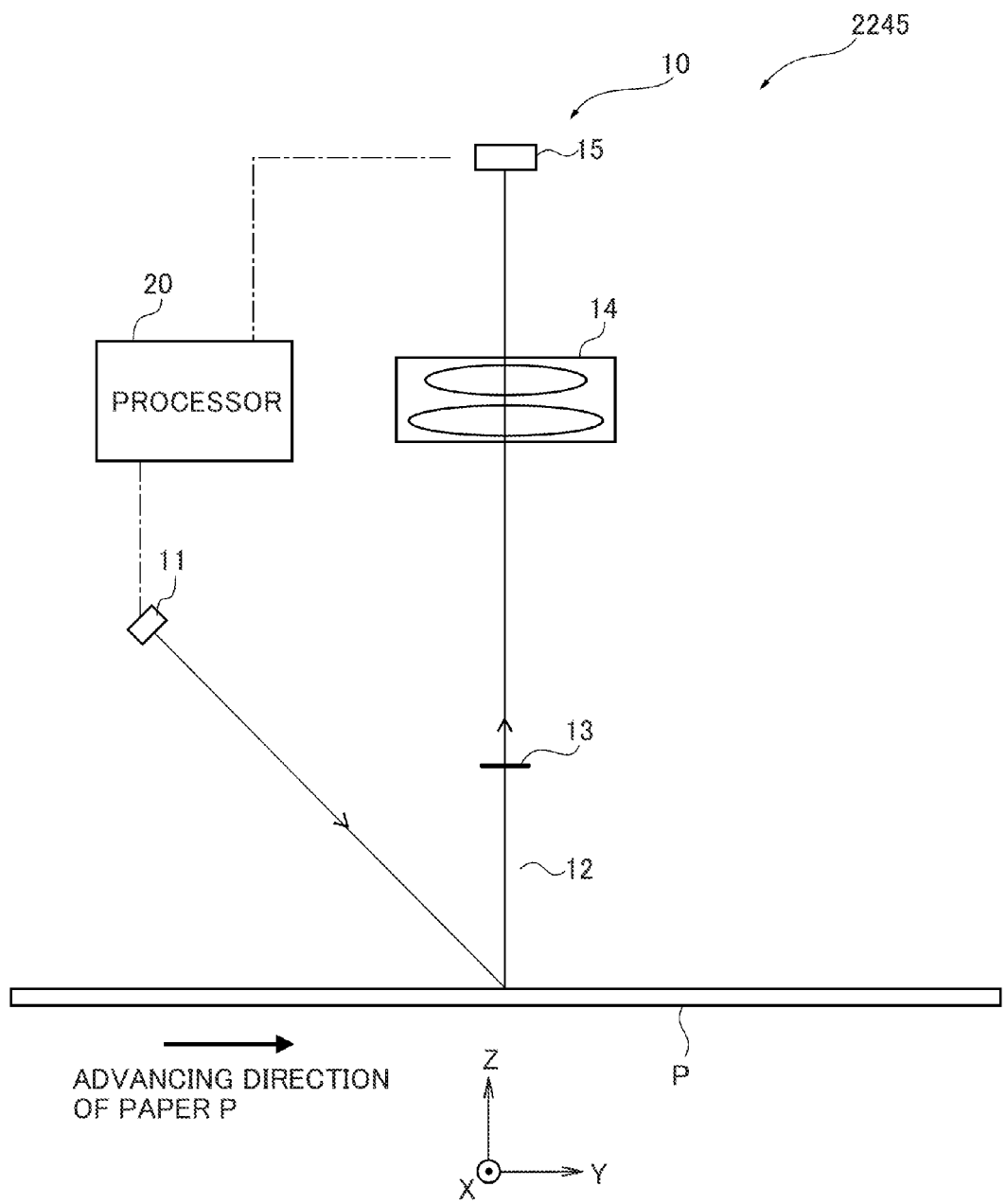
FIG. 5 shows the structure of an image quality detector.

FIG. 5 shows an example of the image quality detector 2245. It includes a spectrometer 10 and a processor 20. A toner image is fused on the surface (+Z side) of a paper P.

The spectrometer 10 is placed on +Z side of the paper P and includes a light source unit 11, an imaging system 14 as imaging element, and a spectroscopic unit 15.

The operation of the spectrometer 10 is as follows. First, the surface of the paper P is irradiated with a light beam from the light source unit 11. The light beam reflected by the paper P is incident on the imaging system 14. An image formed by the imaging system 14 is dispersed and received by the spectroscopic unit 15.

Figure 6A:
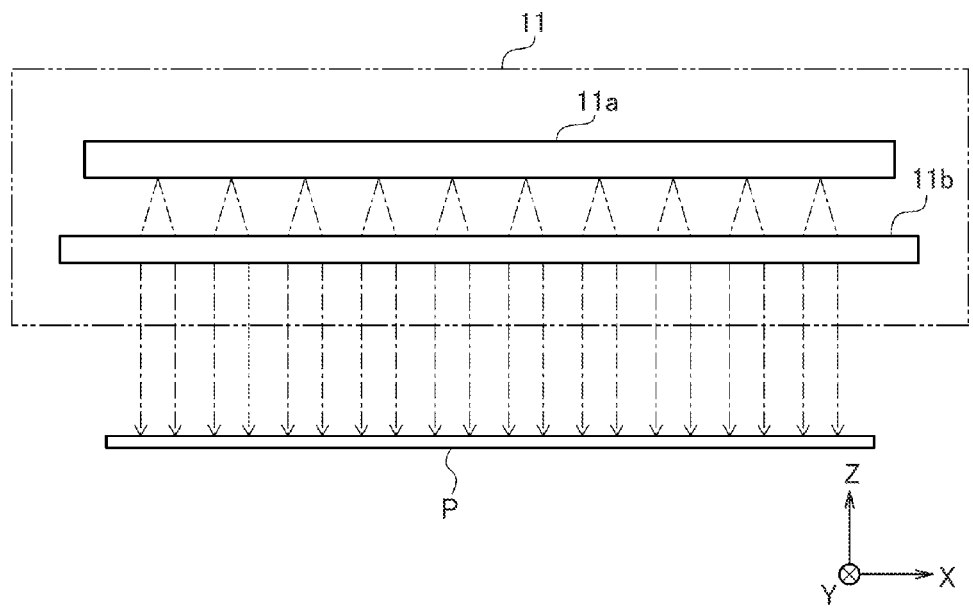
FIGS. 6A, 6B show the structure of a light source unit.
Figure 6B:
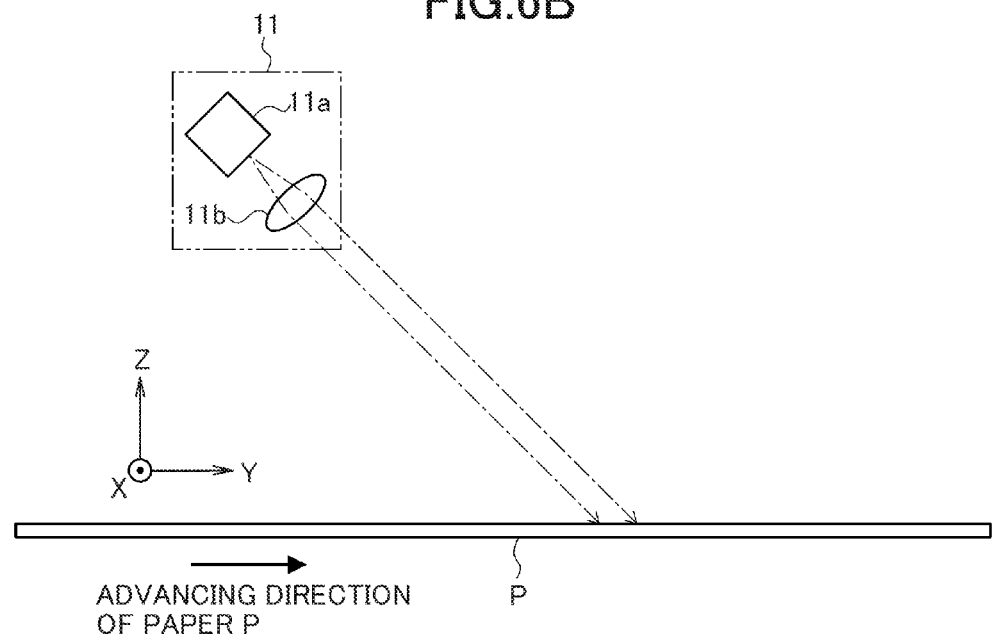

The elements of the spectrometer 10 are described. The light source unit 11 is disposed on −Y axis side separately from the imaging system 14 and spectroscopic unit 15. The light source unit 11 includes, for example, an LED array 11a and a collimate lens array 11b as shown in FIGS. 6A, 6B.

The LED array 11a includes light emitting devices (LED) arranged along X axis. Each LED emits a white light beam with intensity in almost the entire visible light range, and is controlled to turn on and off by the processor 20.

In replace of the LED array, a fluorescent lamp as a cold-cathode tube or other lamps can be used. It is preferable for a light source to emit light in a wavelength range necessary for spectroscopy and be able to evenly illuminate the entire target area.

The collimate lens array 11b includes collimate lenses in association with the LEDs. They are arranged on the optical paths from the LEDs, respectively to convert the white light beams to parallel beams to illuminate the surface of the paper P. That is, the light source unit 11 projects a linear light beam whose longitudinal direction is along X axis.

The white light beams from the light source unit 11 are set to be incident at a certain angle (45 degrees, for example) on the paper P in YZ plane in FIG. 6B. Herein, the light diffused by the surface of the paper P is referred to as reflected beam.

Returning to FIG. 5, the imaging system 14 is placed on +Z side of the paper P, and it is comprised of two convergent lenses for example, to allow the incident light to be converged on the incident surface of the spectroscopic unit 15.

The imaging system 14 owns an image-space telecentric optical property, for example. The telecentric optical property is such that the optical axis and a principal ray are considered to be parallel on one side of a lens. In a telecentric optical system a principal ray is parallel to the optical axis only on an image plane. Thus, the principal ray of light from the imaging system 14 is approximately parallel to the optical axis or Z axis.

Figure 7A:
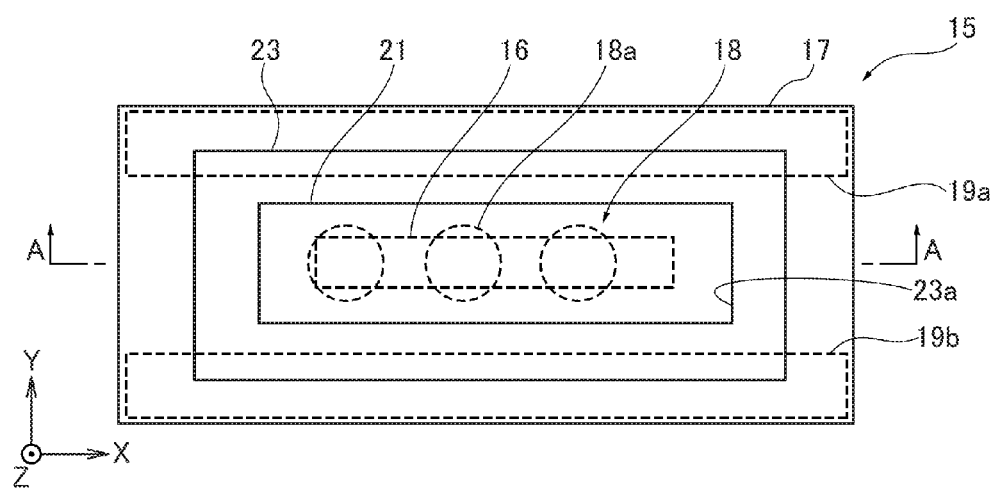
FIGS. 7A, 7B show the structure of a spectroscopic unit.
Figure 7B:
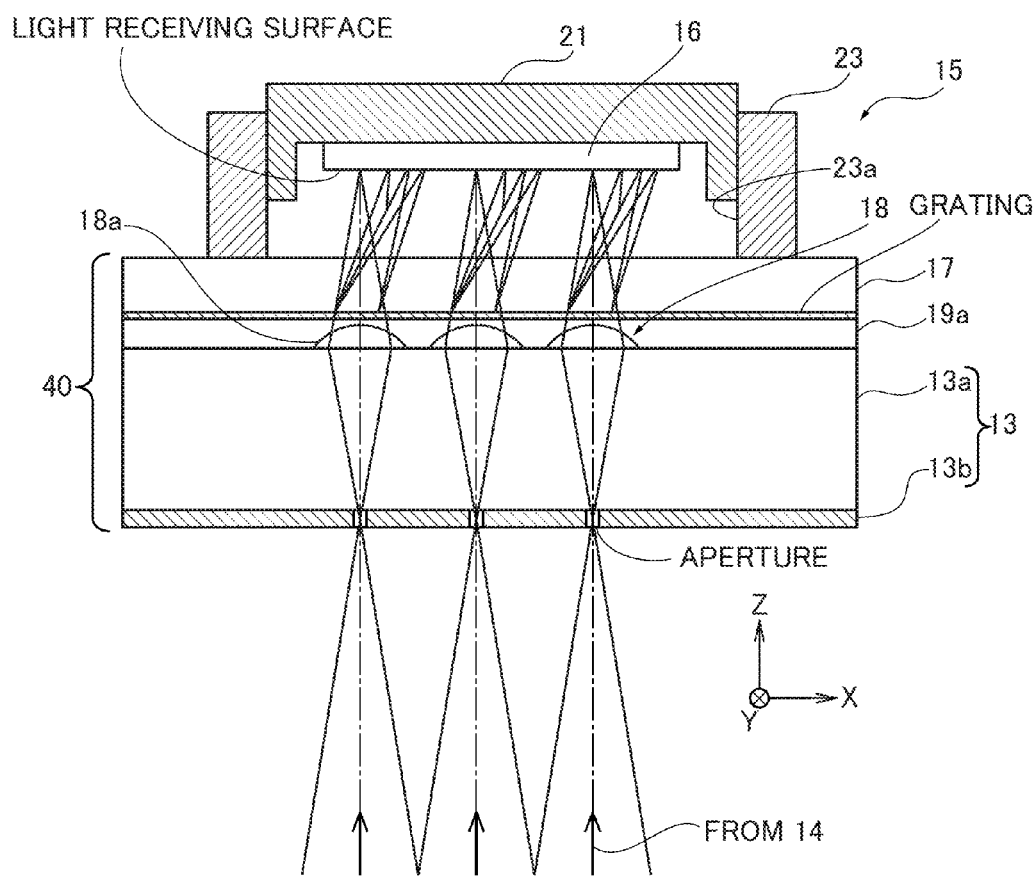

FIG. 7A is a top plan view of the spectroscopic unit 15 while FIG. 7B is a cross section view of the same along the A to A line in FIG. 7A. The spectroscopic unit 15 in FIG. 7A, 7B includes an optical element 13 with apertures, a micro lens array 18 as imaging element, a diffraction element 17, a linear sensor 16 as light receiving element, a pair of spacers 19a, 19b, and a bonding element 23. The optical element 13, micro lens array 18, and diffraction element 17 constitute a spectral element.

The optical element 13 is disposed on the path of the reflected beam via the imaging system 14, and includes a transparent substrate 13a made of an optical glass with even thickness and an optical plate 13b attached on −Z side surface of the transparent substrate 13a by way of example. The −Z side surface of the optical plate 13b is an incidence surface of the optical element 13 and the spectroscopic unit 15. Three apertures, for example, are formed in the optical plate 13b with a certain interval along X axis.

Among the reflected beam from the imaging system 14, only the lights incident on the apertures of the optical plate 13b enter the transparent substrate 13a and are diffused in +Z direction therein. A distance between the centers of the two neighboring apertures along X axis is referred to as aperture pitch.

The apertures can be either pinholes or slits and the shape thereof can be rectangular or elliptical or other shapes in addition to circular. The optical element 13 can be a blackened metal plate with apertures or a glass plate which is coated with a black material of a certain shape such as chrome, carbon-containing resin.

The micro lens array 18 includes three micro lenses 18a, for example. The micro lenses 18a are mounted on the exit surface of the optical element 13 or the +Z side surface of the transparent substrate 13a in accordance with the positions of the corresponding apertures. That is, they are placed on the paths of the reflected beams having passed through the corresponding apertures. The thickness of the transparent substrate 13a is set so that the light beams having passed through the apertures can be incident on the micro lenses 18a. The optical axis of each micro lens 18a is parallel to Z axis.

The light beams travel diffusively inside the transparent substrate 13a, are incident on the corresponding micro lenses 18a and converged. A distance between the centers of the two neighboring micro lenses along X axis is referred to as lens pitch.

The diffraction element 17 is fixed on the transparent substrate 13a of the optical element 13 on +Z side of the micro lens array 18 via a pair of spacers 19a, 19b. It is placed on the paths of light beams via the micro lens array 18, and made of an optical glass with an incidence (−Z side) surface on which a sawtooth grating is formed. A distance between the centers of two neighboring sawteeth is referred to as grating pitch.

The diffraction angle θm of the diffraction element 17 is expressed by the following equation:

$$\sin \theta m = m\lambda/p + \sin \alpha$$

where p is a grating pitch, α is an incidence angle of reflected beam on the diffraction element 17, and λ is a wavelength of light contained in the reflected beam. The light beam with the wavelength λ is diffracted at the angle θm.

The sawtooth grating can increase the optical intensity of $+1^{st}$ order diffracted images. The unevenness of grating can be stepwise.

The light beams diffracted by the diffraction element 17 travel in different directions according to wavelengths. That is, the reflected beams are diffracted by the diffraction element 17 by wavelengths.

The linear sensor 16 is fixed on an inner bottom surface of a package 21 as a ceramic open box, for example. The package 21 is joined with the diffraction element 17 via a bonding element 23 so that an aperture side faces −Z axis. The linear sensor 16 is placed in the package 21 at a position on which an image of a $+1^{st}$ order diffracted light (hereinafter, $+1^{st}$ order diffracted image) is formed, and includes, for example, six pixels 16a as light receiving areas arranged along X axis in FIG. 9A. Each pixel outputs a signal to the processor 20 in accordance with a light receiving amount. A distance between the centers of the two neighboring pixels is referred to as pixel pitch.

Figure 8:
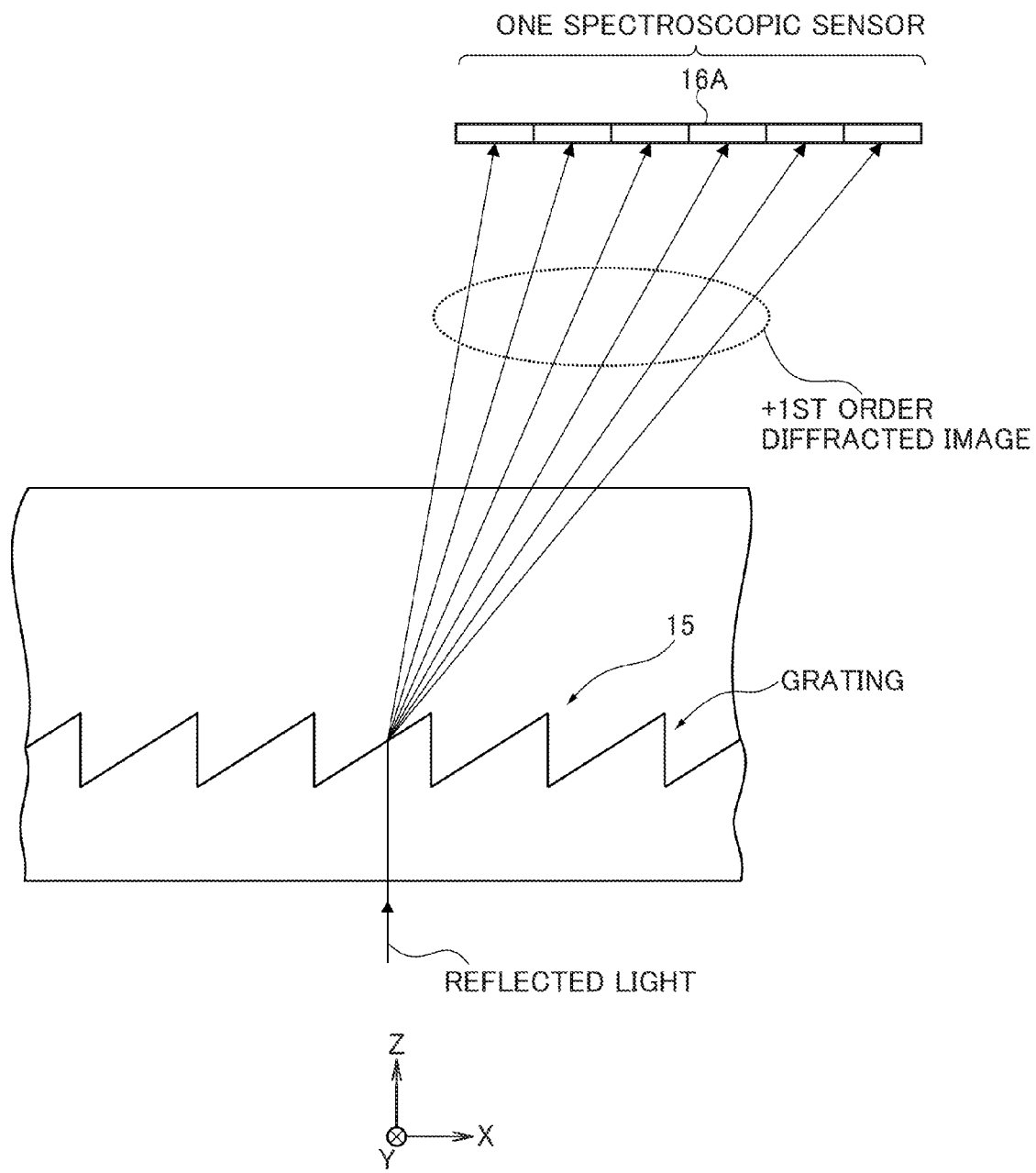
FIG. 8 shows the structure of a spectroscopic sensor.
Figure 9A:
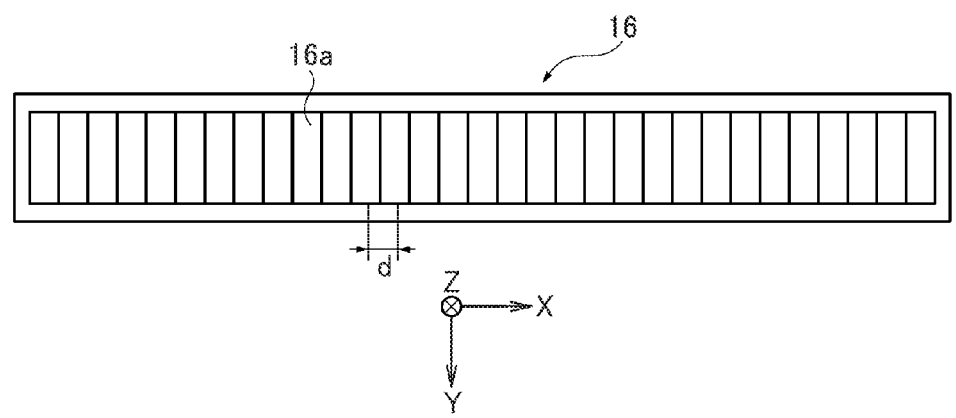
FIG. 9A shows the structure of a linear sensor and FIG. 9B shows a relative position between the diffraction element and the linear sensor.
Figure 9B:
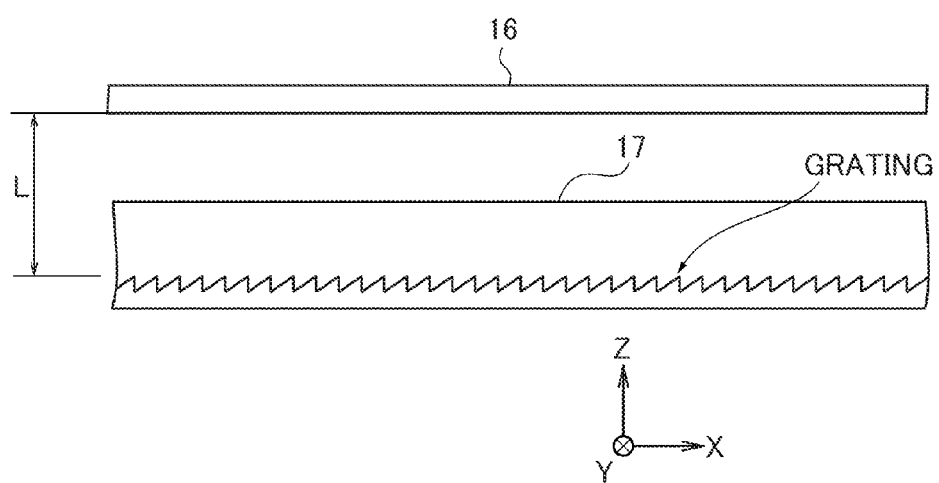

For instance, if the pixel pitch d of the linear sensor is 10 μm, the grating pitch p of the diffraction element 17 is 10 μm, and the distance L between the grating of the diffraction element 17 and linear sensor 16 is 2 mm in FIG. 9B, the reflected beam having passed through a single aperture of the optical element 13 is received at the six pixels 16a according to wavelengths, as shown in FIG. 8 by way of example. Thus, the six pixels constitute a single spectroscopic sensor.

Figure 10:
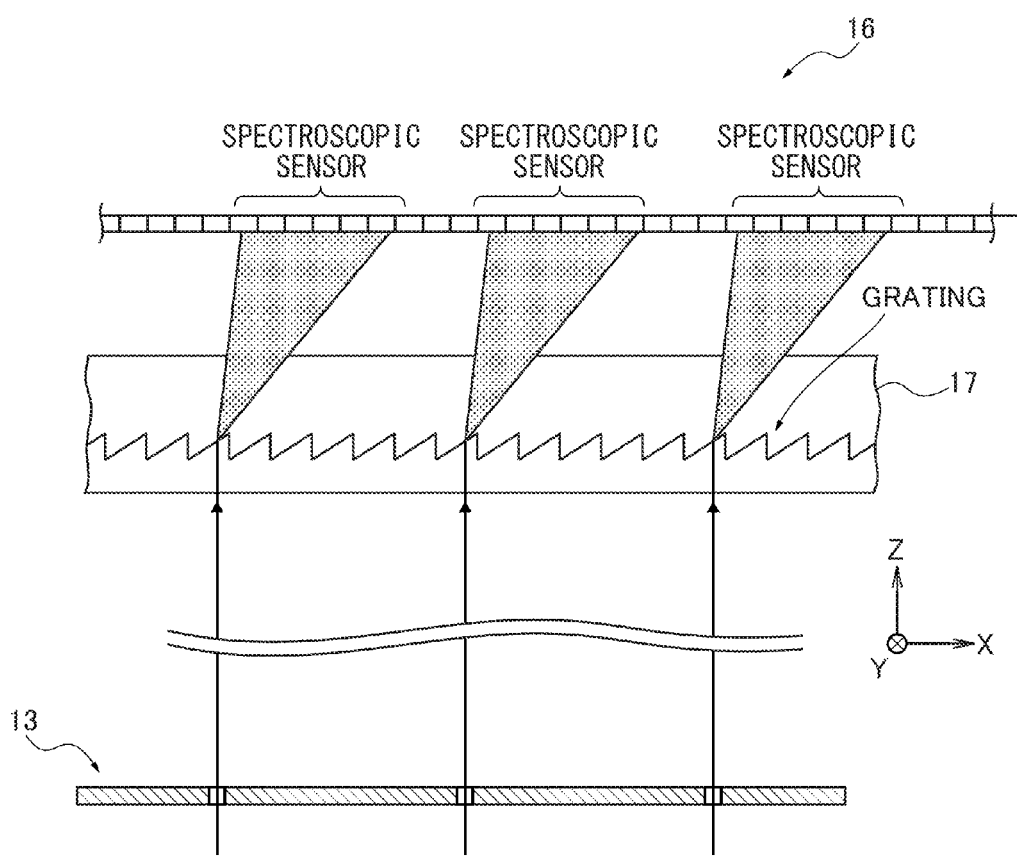
FIG. 10 shows the spectral wavelength of the diffraction element.

That is, the linear sensor 16 is an aggregate of spectroscopic sensors in FIG. 10 which individually receive diffracted images having transmitted through different apertures. FIG. 10 shows three spectroscopic sensors by way of example, however, the present invention should not be limited thereto. A large number of spectroscopic sensors can be provided in a single linear sensor. For instance, with use of a linear sensor having 1,024 pixels, 102 spectroscopic sensors can be configured.

In the following a wavelength range of a light beam received at a single pixel is referred to as a band and dispersing the $+1^{st}$ order diffracted image into different bands is referred to as multi-band spectroscopy. A relation between the wavelength and optical intensity or reflection rate of the reflected beam is referred to as reflected beam wavelength spectrum.

Figure 11:
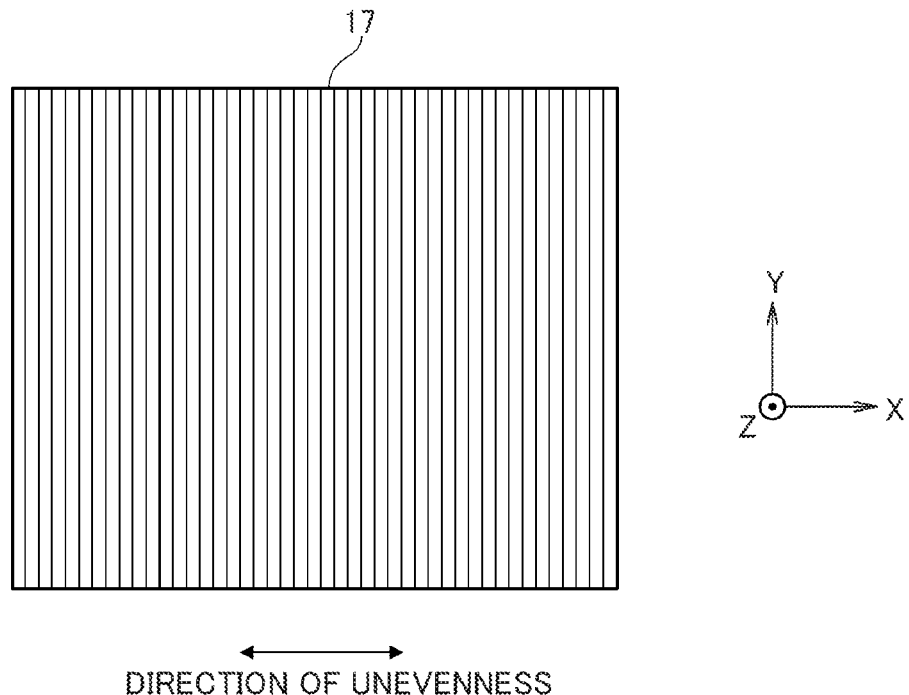
FIG. 11 shows a direction of unevenness on the diffraction element and a crosstalk.
Figure 12:
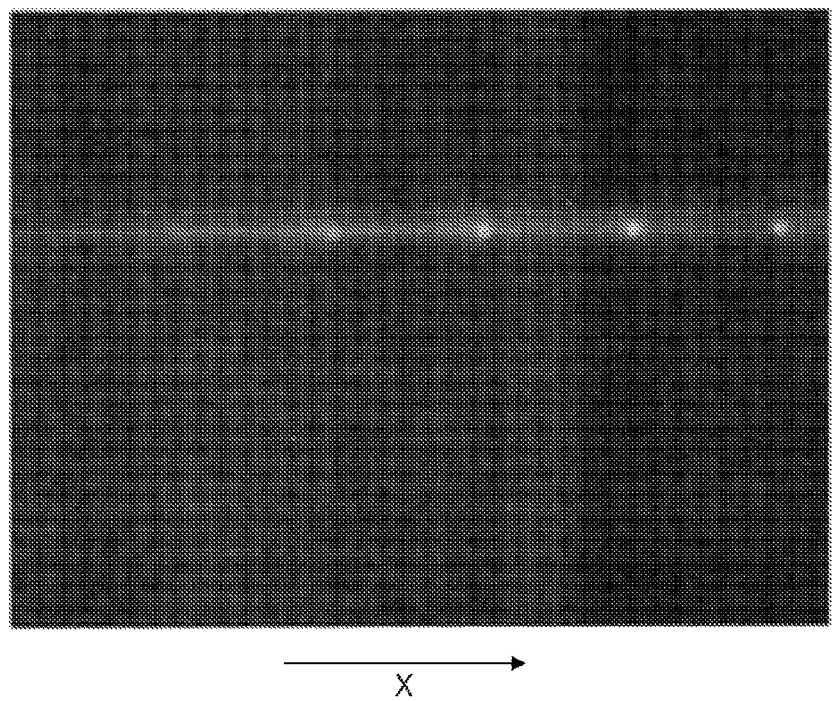
FIG. 12 shows a crosstalk among spectroscopic sensors.

As shown in FIG. 11, the direction of unevenness on the diffraction element 17 is parallel to X axis. There may be a case where $0^{th}$ and $+2^{nd}$ order diffused light beams and diffused light beams of the reflected beams having passed through the neighboring apertures overlap on the linear sensor 16 and cause a crosstalk between the neighboring spectroscopic sensors as shown in FIG. 12. This hinders accurate spectroscopy.

Figure 13A:
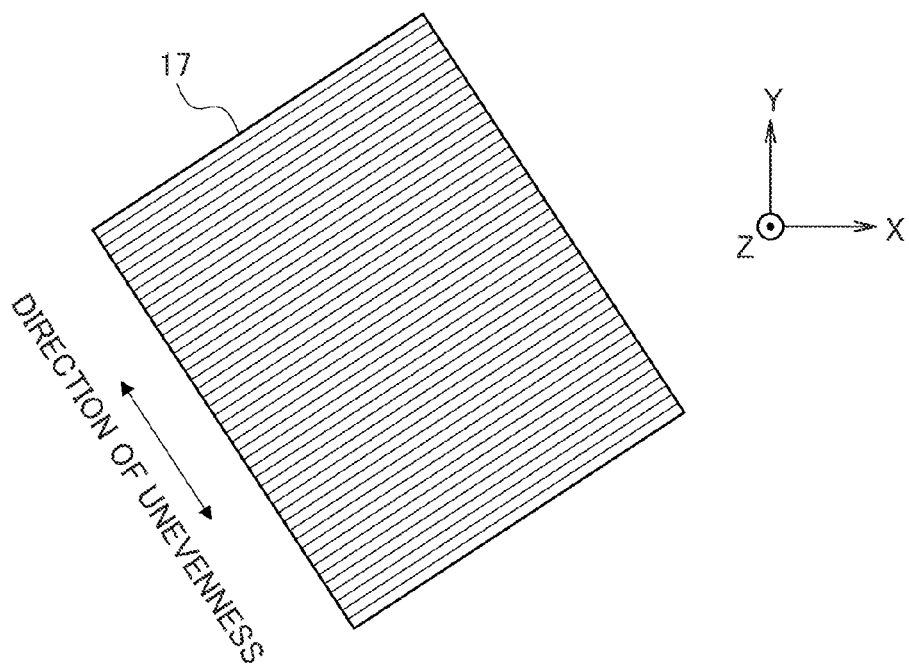
FIGS. 13A, 13B show the inclination of a direction of unevenness on the diffraction element.
Figure 13B:
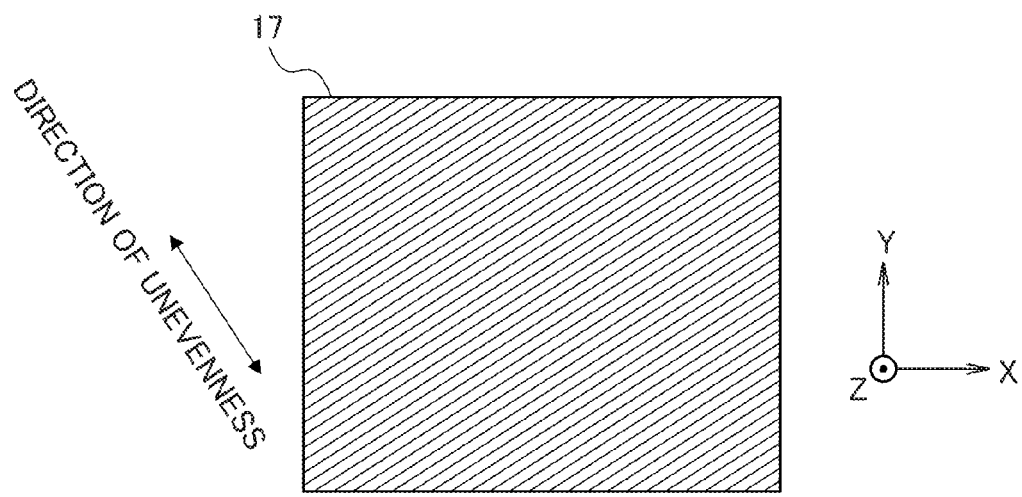
Figure 14:
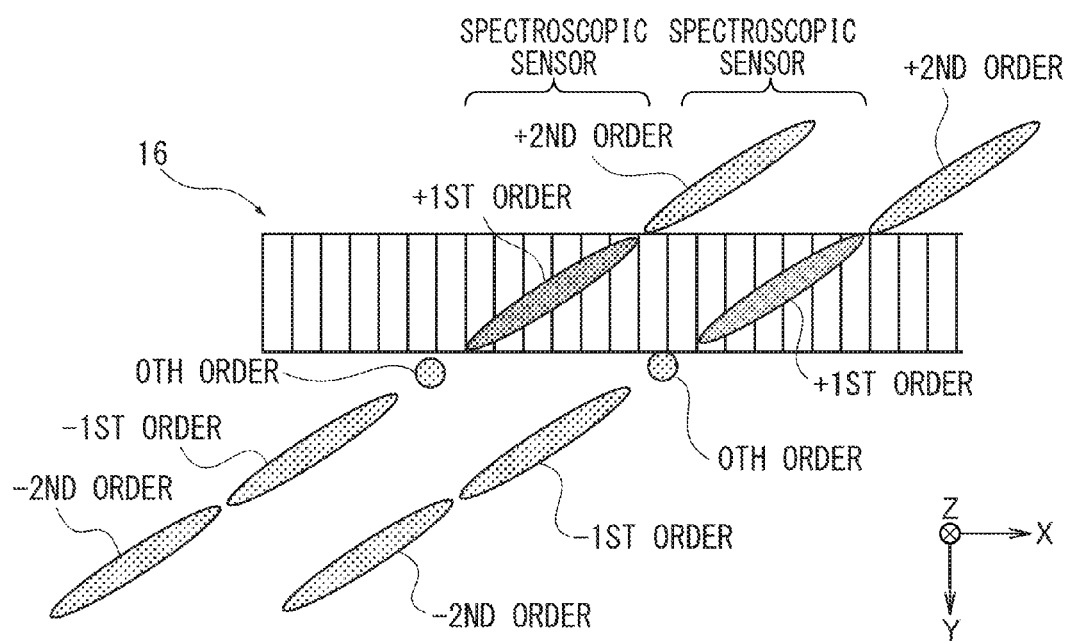
FIG. 14 shows the alignment of diffracted images.
Figure 15:
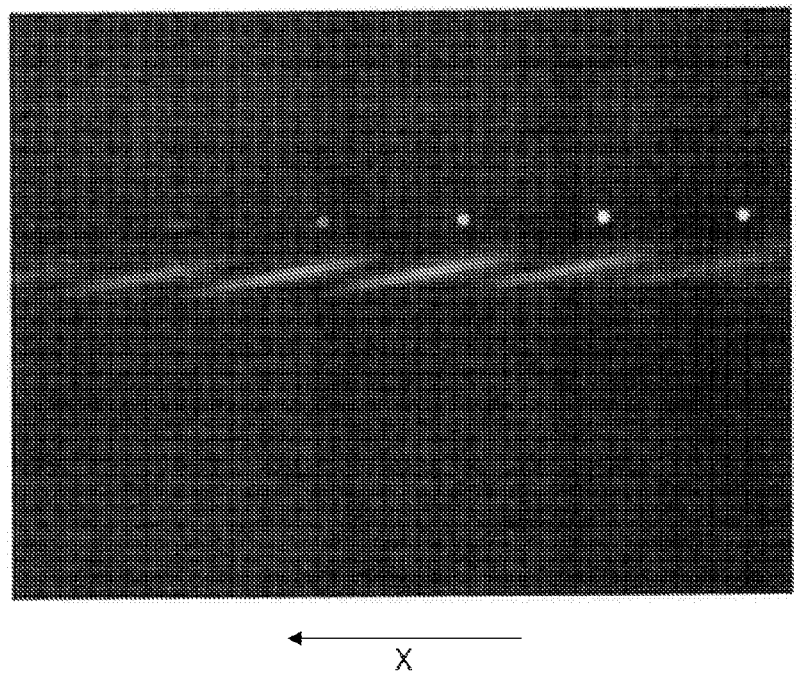
FIG. 15 shows a crosstalk resolved.

In view of this, in the present embodiment the diffraction element 17 is rotated about the axis parallel to the Z axis to incline the sawtooth unevenness at 30 to 45 degrees relative to the X axis in which the pixels 16a of the linear sensor 16 are aligned, as shown in FIG. 13A. Thereby, each spectroscopic sensor can receive only $+1^{st}$ order diffracted images. Alternatively, a diffraction element with unevenness inclined relative to sides in FIG. 13B can be used. FIGS. 14, 15 show a relative position between the respective diffracted images and the linear sensor 16 when the direction of unevenness is inclined relative to the X axis by about 10 degrees. In FIG. 14 the linear sensor 16 receives only the $1^{st}$ order diffracted images and does not receive unnecessary diffracted images as $-1^{st}$, $0^{th}$, $2^{nd}$ order diffracted images. Also, all the $1^{st}$ order diffracted images are in the areas of the spectroscopic sensors. It can be configured to receive $-1^{st}$ and $+2^{nd}$ order diffracted images instead of $+1^{st}$ order diffracted images by adjusting the respective elements.

In the multi-band spectroscopy, the larger the number of bands, the more accurate wavelength spectrum of reflected beam can be obtained. However, the number of pixels of the linear sensor is unchanged, so that the number of pixels used for one spectroscopic sensor increases as the number of bands increases, reducing the number of spectroscopic sensors and the number of measure points.

In view of this, the number of bands is limited to a minimum and the processor 20 is configured to estimate the reflected beam wavelength spectrum by Wiener filtering in the present embodiment. Various methods are available for estimating the reflected beam wavelength spectrum, for example, disclosed in pp. 154 to 157, "Analysis and Evaluation of Digital Color Images" by University of Tokyo Press.

The controller 2090 is configured to conduct image process control when at power-on, 1) the photoreceptor drums are stopped over six hours, 2) the internal temperature of the device is changed by 10 degrees or more, or 3) the relative humidity of the device is changed by 50% or more, as well as during printing, 4) the number of prints reaches a predetermined value, 5) the rotation number of the develop roller reaches a predetermined value, or 6) the running distance of the transfer belt is a predetermined value.

The controller 2090 instructs the processor 20 to conduct spectroscopy according to an image resolution and at a good timing for image process control.

The controller 2090 acquires color information for each measure position on the basis of a result of the calculation of the processor 20. Wavelength spectrum data on colors are stored in the memory of the controller 2090.

Upon detection of a color variation or unevenness in a single paper sheet, the controller 2090 controls the amount of light from the light source of the optical scanner 2010. Upon detection of a color variation over two paper sheets, it controls at least any of develop bias, fuse temperature, and light amount from the light source in each scanning.

Meanwhile, with a displacement of the relative positions among the optical element, micro lens array, diffraction element and linear sensor over time or due to oscillation or temperature change, the relative position of the diffracted images and the linear sensor is also displaced, affecting the accuracy of spectroscopy. To acquire a spectral characteristic at a sufficient accuracy, the relative position of these elements needs to be stable by several nm in wavelength direction in the range of visible light in a wavelength bandwidth of 400 nm to 700 nm. For instance, to acquire a spectral characteristic with six pixels, a stability of one-several tenth of a pixel width is needed along the alignment of the pixels.

Particularly, an LED light source with a blue LED to project a white light beam greatly affects spectroscopic accuracy. The light from the blue LED is narrow in the wavelength bandwidth in comparison with the tristimulus value of a color matching function as a spectral sensitivity characteristic of the human eye so that the displacement of the relative positions of the elements greatly affects the calculation of the tristimulus value and the color of a target object (for example, value of CIE L*a*b). The white LED with a blue LED is advantageous in terms of relatively inexpensive price, long life span, and stability. It can be industriously very applicable only if the displacement is prevented.

For the purpose of preventing the displacement of the relative positions, in the present embodiment the optical element 13, micro lens array 18, diffraction element 17, and linear sensor 16 are unitized by mounting the micro lens array 18 on the optical element 13, fixing the optical element 13 and diffraction element 17 via the pair of spacers 19a, 19b, and fixing the package 21 and diffraction element 17 via the bonding element 23, as described above.

Specifically, each spacer is comprised of a plate long along X axis in FIGS. 7A, 7B. The pair of spacers 19a, 19b are bonded on both ends of the +Z side surface of the transparent substrate 13a via an adhesive, respectively. The micro lens array 18 is placed between the pair of spacers 19a, 19b. The spacers are the same in thickness and the thickness is longer than the length of the micro lens 18a along the optical axis or Z axis.

The spacers are preferably made from a material such as an optical glass with a coefficient of thermal expansion very close to or the same as that of the diffraction element 17 and the transparent substrate 13a. This can reduce the warpage or bending due to a difference in the coefficient of thermal expansion of materials relative to a temperature change.

The diffraction element 17 is fixed on the +Z side surfaces of the pair of spacers 19a, 19b with an adhesive and the diffraction element 17 and optical element 13 are fixed at certain relative positions.

The bonding element 23 is made up of a plate long along X axis by way of example, and includes at the center a rectangular aperture 23a long along X axis and four inner side surfaces.

The bonding element 23 is preferably made from a material with a coefficient of thermal expansion very close to or the same as that of the diffraction element 17 and the package 21. This can reduce the warpage or bending due to a difference in the coefficient of thermal expansion of materials relative to a temperature change.

The outer shape of the package 21 is cuboid with an open −Z side and four side surfaces, and slightly smaller than the rectangular aperture 23a of the bonding element 23 and fitted thereinto. The outer side surfaces of the package 21 and the inner side surfaces of the bonding element 23 are bonded approximately in parallel with an adhesive. A first virtual plane including the bonded surfaces of the bonding element 23 is orthogonal to the XY plane. The amount at which the package 21 is inserted into the rectangular aperture 23a is set so that the light receiving surface of the linear sensor 16 is positioned in the vicinity of the focal point of each micro lens 18a.

The −Z side surface of the bonding element 23 is fixed in parallel on the +Z side surface of the diffraction element 17 with an adhesive at a set position relative to the Z axis and a direction orthogonal to and around the Z axis, so that the $+1^{st}$ order diffracted images from the diffraction element 17 are received at the corresponding pixels of the linear sensor 16. A second virtual plane including the bonded (−Z side) surface of the bonding element 23 is approximately in parallel to the XY plane. Thus, the first and second virtual planes are approximately orthogonal to each other.

The optical element 13, micro lens array 18, diffraction element 17 and linear sensor 16 are integrated in a certain relative position. In the following the optical element 13, micro lens array 18, pair of spacers 19a, 19b, and diffraction element 17 are collectively referred to as spectroscopic unit 40.

Next, the assembly of the spectroscopic unit 15 is described. The relative position of the spectral unit 40 and linear sensor 16 needs to be adjusted.

In the present embodiment the direction of the unevenness of the diffraction element 17 is inclined relative to the X axis at a certain angle, and the $-2^{nd}$ order to $+2^{nd}$ order diffracted images of a single light beam are aligned in a direction orthogonal to the unevenness direction in FIG. 14. Therefore, to receive only the +1st order diffracted images at the spectroscopic sensors of the linear sensor 16, the spectral unit 40 and linear sensor 16 have to be relatively adjusted in position relative to the Z axis or the optical axis of the micro lens 18a and a direction orthogonal to and around the Z axis. This adjustment relative to the Z axis includes adjusting the size of the +1st order diffracted image in accordance with a variation in focal length of the micro lenses 18a resulting from curvature errors during manufacturing, for instance.

The assembly process of the spectroscopic unit 15 is described by way of example, referring to FIGS. 16A to 16D. The spectroscopic unit 15 is assembled manually by an operator. In the following αβγ three-dimensional coordinate system is used. A vertical direction is defined to be γ axis (+γ being upward), and a direction orthogonal to γ axis is α axis and a direction orthogonal to γ and α axes is β axis.

Figure 16A:
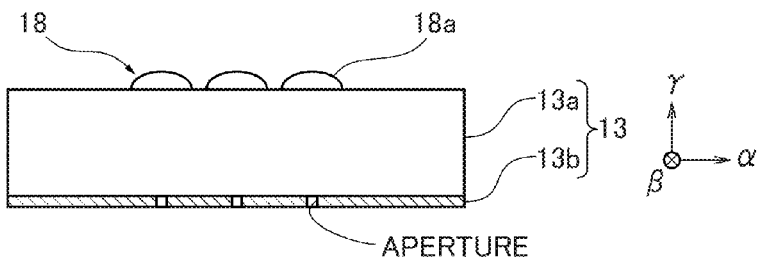
FIGS. 16A to 16D show the assembly process of the spectroscopic unit according to the first embodiment.

First, in FIG. 16A the optical element 13 is placed with the optical plate 13b on −γ side and the apertures aligned on α axis. The micro lenses 18a are bonded on the +γ side surface of the optical element 13 at positions in association with the apertures.

Figure 16B:
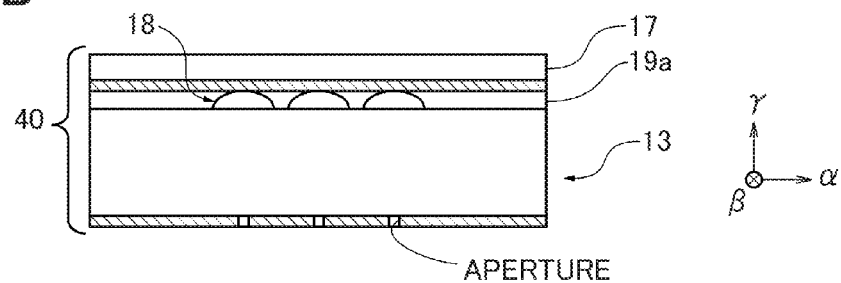

Then, in FIG. 16B both ends of the +γ side surface of the optical element 13 are bonded on the −γ side surfaces of the spacer 19a, 19b with an adhesive while the +γ side surfaces of the spacer 19a, 19b are bonded on the −γ side surface of the diffraction element 17 with an adhesive. Thus, the optical element 13 and diffraction element 17 are integrated via the spacer 19a, 19b to create the spectroscopic unit 40.

Figure 16C:
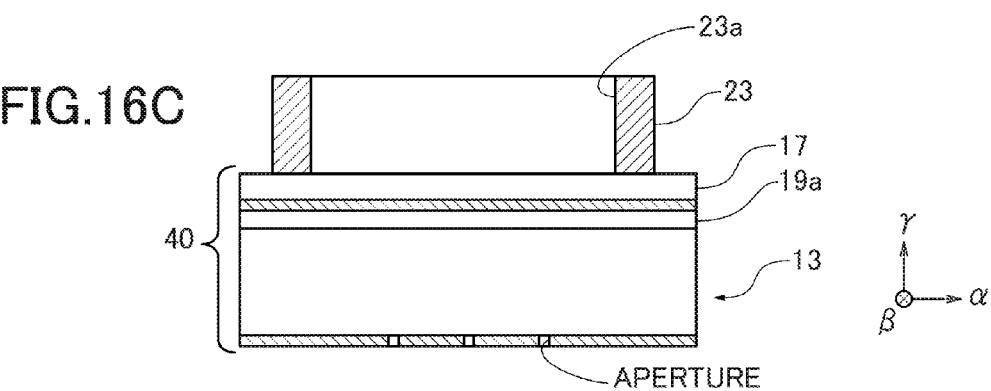

In FIG. 16C the bonding element 23 is then placed on the spectroscopic unit 40, that is, the +γ side surface of the diffraction element 17.

Figure 16D:
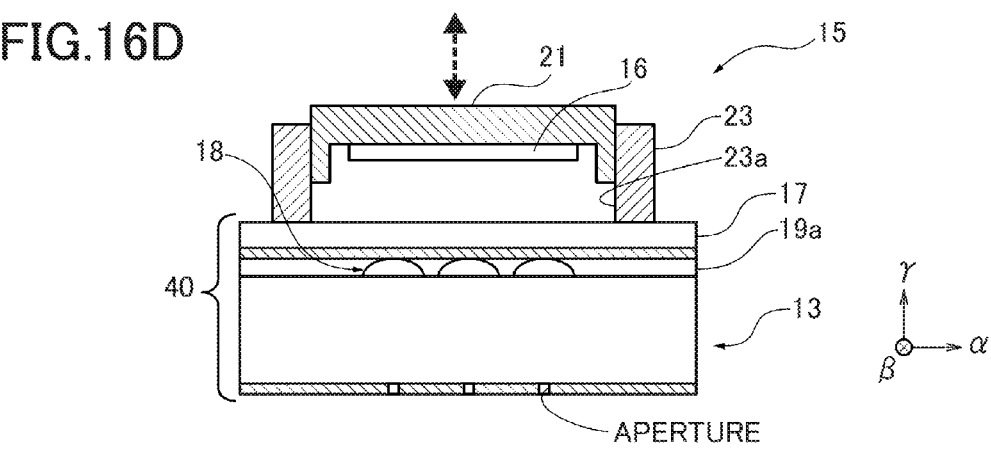

Next, in FIG. 16D the linear sensor 16 is fixed on the inner bottom surface of the package 21 with an adhesive and the package 21 is fitted into the rectangular aperture 23a of the bonding element 23.

Alternatively, the bonding element 23 can be placed on the spectral unit 40 after the package 21 containing the linear sensor 16 is fitted into the bonding element 23. As described above, the spectral unit 40 and the linear sensor 16 are assembled by integrating the diffraction element 17 and the linear sensor 16. The diffraction element 17 and the package 21 are integrated via the adhesive.

In FIG. 16D the first virtual plane including the bonded surface of the bonding element 23 and package 21 is approximately orthogonal to the second virtual plane including the bonded surface of the bonding element 23 and spectral unit 40 or diffraction element 17.

Figure 17:
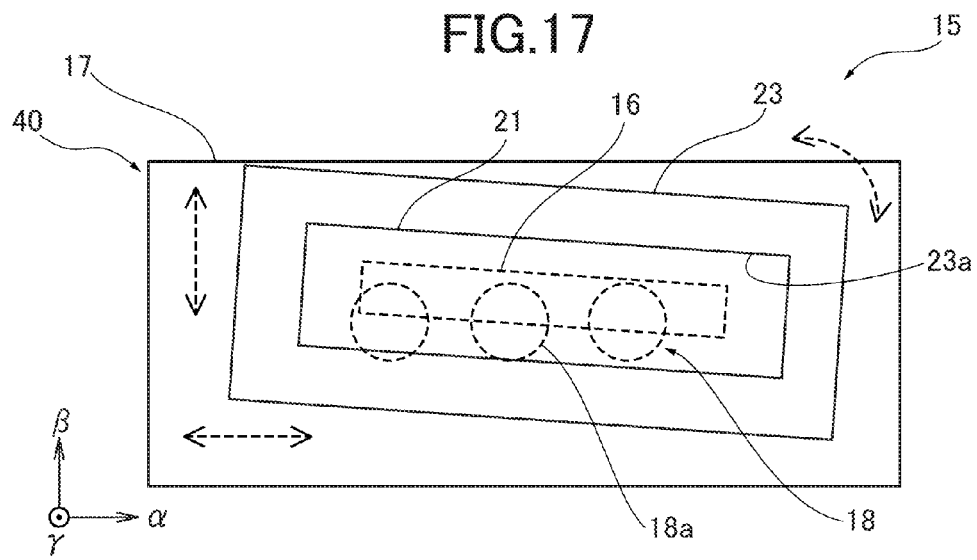
FIG. 17 shows the assembly process of the spectroscopic unit.

In this case with the bonding element 23 placed on the spectroscopic unit 40, the parallel movement of the bonding element 23 and spectral unit 40 is limited to the directions orthogonal to γ axis (α, β axes), and the rotation thereof is limited to around γ axis in FIG. 17.

Further, with the bonding element 23 fitted into the package 21, the parallel movement thereof is limited to γ axis alone and they cannot be rotated in FIG. 16D.

Thus, the package 21 and spectral unit 40 can be moved in parallel only on γ axis and the directions orthogonal to γ axis and rotated about γ axis.

When a white light beam is projected to the spectral unit 40 or optical element 13 from −γ axis, the linear sensor 16 receives diffracted images. The positions of the spectroscopic sensors are adjusted to receive only the +1st order diffracted images by relatively moving the package 21 and bonding element 23 along γ axis, relatively moving the bonding element 23 and spectral unit 40 in the direction orthogonal to γ axis, and relatively rotating the bonding element 23 and spectral unit 40 about γ axis while the output signals from the six pixels of each spectroscopic sensor are monitored. In the present embodiment a relative movement includes moving one still object relative to the other object and moving both of the objects. Similarly, a relative rotation includes rotating one object relative to the other object and rotating both of the objects.

As shown in FIG. 14, since the +1st order diffracted images are aligned along X axis, the positioning of the bonding element 23 and spectral unit 40 along α axis is not important to receive the +1st order diffracted images alone at the spectroscopic sensors.

Next, an example of the positioning thereof along γ axis, around γ axis and the direction orthogonal to γ axis is described. First, light beams are projected to a white diffuse plate via band filters with different wavelength bands, and reflected beams are guided to the linear sensor 16 through the imaging system 14, optical element 13, micro lens array 18, and diffraction element 17. If a signal of a $0^{th}$ order diffracted image is outputted from a single pixel and a signal of a +1st order diffracted image is outputted from another pixel, the package 21 and the bonding element fitted with each other are relatively moved along γ axis, and the bonding element 23 and the spectral unit 40 are relatively moved along β axis to prevent the output of the $0^{th}$ order diffracted image and output the +1st order diffracted images from six pixels, for example. Further, to output the same quality signals from all the spectroscopic sensors (three, for instance), the bonding element 23 and spectral unit 40 abutting with each other are relatively rotated around γ axis.

After the spectral unit 40 and package 21 are positioned as above, the outer side surface of the package 21 and the inner side surface of the bonding element 23 are bonded with an adhesive, and the −γ side surface of the bonding element 23 and the +γ side surface of the spectral unit 40 are bonded with an adhesive to create a spectroscopic unit 15.

The adhesive for bonding the spectral unit 40 and bonding element 23 and the bonding element 23 and package 21 is preferably a ultraviolet curable resin and the bonding element 23 is preferably configured to transmit at least an ultraviolet beam. After the spectral unit 40 and package 21 are positioned, a ultraviolet curable resin is injected between the outer side surface of the package 21 and the inner side surface of the bonding element 23 and between the −γ side surface of the bonding element 23 and the +γ side surface of the spectroscopic unit 40, and irradiated with an ultraviolet beam, to bond the bonding element 23 and spectroscopic unit 40. Thereby, the thickness of the adhesive can be minimized, and the elements can be prevented from being displaced due to vibration arising from a poor strength of the adhesive layer and the coefficient of thermal expansion thereof.

Likewise, the adhesive for bonding the optical element 13 and spacers 19a, 19b and the spacers 19a, 19b and diffraction element 17 is preferably an ultraviolet curable resin and at least one of the spacers 19a, 19b is configured to transmit at least a ultraviolet ray. The same effects as above can be also attained.

The spectrometer 10 according to the first embodiment includes the light source unit 11 to project a light beam to the paper P, optical element 13 with apertures disposed on the path or a reflected beam by the paper P, micro lens array 18 with micro lenses 18a individually arranged on the paths of light beams having transmitted through the apertures, diffraction element 17 disposed on the paths of light beams from the micro lenses 18a, and linear sensor 16 with light receiving areas 16a to individually receive the diffracted images formed by the diffraction element 17.

As configured above, the reflected beams from the paper P are incident on the diffraction element 17 through the apertures and micro lens 18a. The diffraction element 17 forms the diffracted images of the light beams and these images are received at the respective light receiving areas 16a of the linear sensor 16.

Further, the optical element 13, micro lens array 18, diffraction element 17, and linear sensor 16 are integrated as a unit. This can reduce a displacement of the relative positions among the optical element 13, micro lens array 18, diffraction element 17 and linear sensor 16 over time or due to vibration or temperature change. Accordingly, the spectrometer 10 can stably, accurately measure the wavelength spectrum of reflected beam or stably perform spectroscopy.

Further, even with use of a white LED with a blue LED for a light source, it can maintain the accuracy of spectroscopy.

Further, the diffraction element 17 is placed so that the spectroscopic sensors of the linear sensor 16 can receive only the +1st order diffracted images, which makes it possible to prevent crosstalk over the neighboring spectroscopic sensors.

Further, owing to the first and second virtual planes orthogonal to each other, when the package 21 is fitted into the bonding element 23 and the bonding element 23 is placed on the spectral unit 40 for the assembly of the spectroscopic unit 15, the parallel movement of the package 21 and spectral unit 40 can be limited to along γ axis and in the direction orthogonal to γ axis, and the rotation thereof can be limited to around γ axis.

The package 21 and spectroscopic unit 40 can be relatively moved along γ axis via the bonding element 23 and along the plane orthogonal to γ axis to easily position them. Accordingly, the spectroscopic unit 15 can be assembled easily and quickly.

Furthermore, the image quality detector 245 includes the spectrometer 10 and the processor 20 to calculate the estimation of the wavelength spectrum of a reflected beam at each measure point on the basis of the output signal of the spectrometer 10.

The controller 2090 is configured to instruct the image quality detector 2245 to detect the quality of an image according to the image resolution at image process control timing. It also adjusts the image generation process on the basis of a result of the detection by the image quality detector 2245. Accordingly, the image forming device 2000 according to the present embodiment can generate images with high quality stably.

Further, it can calculate the tristimulus value XYZ and colorimetric data as CIELAB from the spectral reflectivity of an image printed on the paper P detected by the image quality detector 2245. Accordingly, the image forming device 2000 can monitor a printing process from the colorimetric data to adjust it or stop printing if there is any change in the printing process. Thus, it can generate good images represented in accurate colors stably.

Furthermore, the magnitude relation between the bonding element 23 and package 21 can be reverse so that the bonding element is fitted into the package 21 and bonded with each other.

Further, instead of the spacers 19a, 19b separately arranged along Y axis, an opening in which the micro lens array 18 is placed or a plate with a notch parallel to XY plane can be provided. Alternatively, the spacers extending along Y axis can be separately arranged along X axis.

Moreover, instead of the spacers 19a, 19b, at least one protrusion can be provided on the end of the +Z side surface of the optical element or on the end of the −Z side surface of the diffraction element.

Second Embodiment

A spectroscopic unit according to a second embodiment is described with reference to FIG. 18 and FIGS. 19A to 19C.

Figure 18:
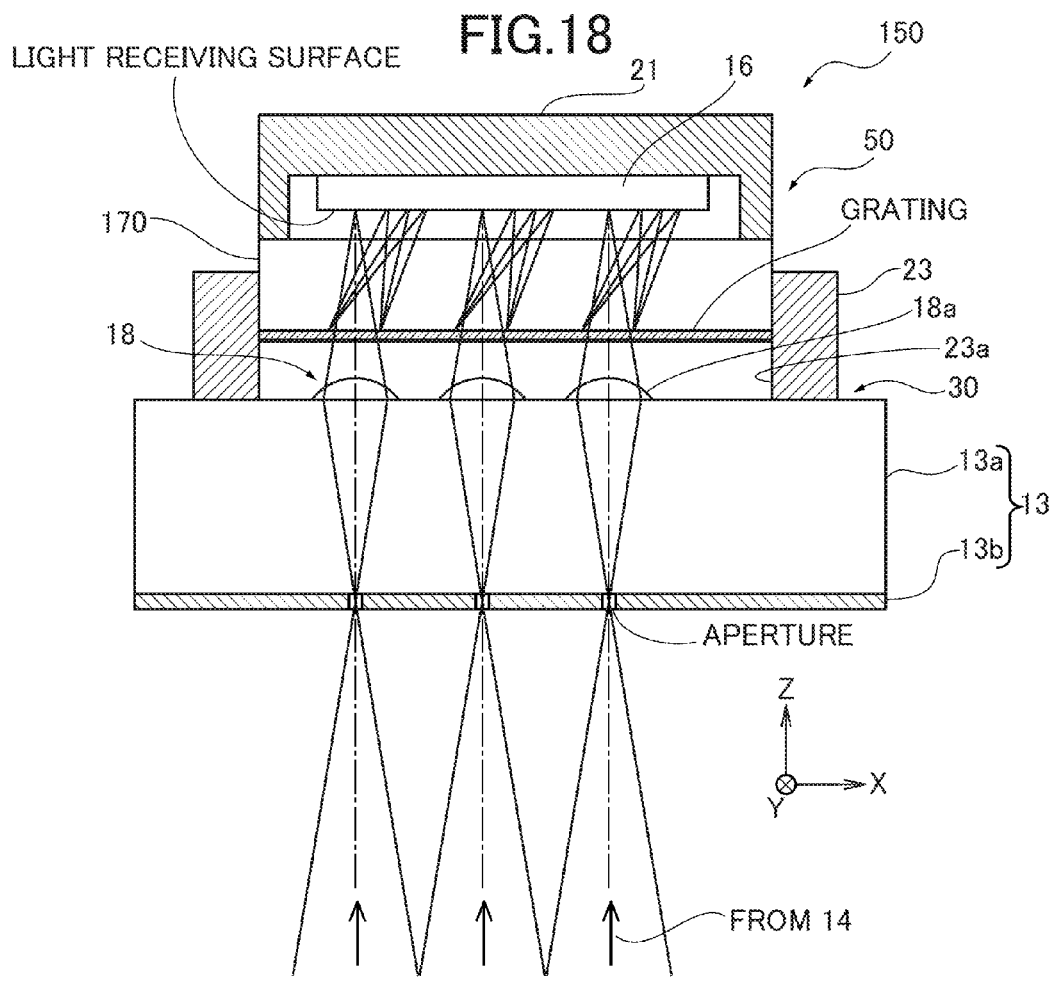
FIG. 18 shows a spectroscopic unit according to a second embodiment.

A spectroscopic unit 150 is differently configured from that 10 in the first embodiment. In FIG. 18 the package 21 containing the linear sensor 16 is directly bonded on a diffraction element 170. The linear sensor 16 and diffraction element 170 is integrally fixed in a certain relative position. The diffraction element 170 and optical element 13 are bonded via the bonding element 23. Thus, the spectroscopic unit 150 is configured without the spacers.

Specifically, the −Z side surface of the package 21 and the +Z side surface of the diffraction element 170 are bonded with an adhesive. That is, the diffraction element 170 and linear sensor 16 are integrally formed. The diffraction element 170 is fitted into the bonding element 23 and bonded with an adhesive with the inner side surfaces of the bonding element and the outer side surfaces of the diffraction element 170 in parallel. The −Z side surface of the bonding element 23 and the +Z side surface of the optical element 13 are bonded in parallel with an adhesive. The outer shape of the diffraction element 170 is a cuboid slightly smaller than the rectangular aperture 23a, seen from +Z axis.

Thus, a third virtual plane including the bonded surface of the bonding element 23 and diffraction element 170 is approximately orthogonal to a fourth virtual plane including the bonded surface of the bonding element 23 and optical element 13.

In the following the optical element 13 and the micro lens array 18 are collectively referred to as lens unit 30 while the diffraction element 170, package 21, and linear sensor 16 are referred to as sensor unit 50.

Figure 19A:
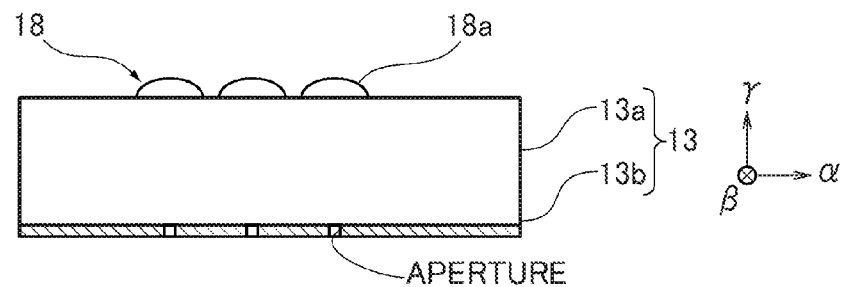
FIGS. 19A to 19C show the assembly process of the spectroscopic unit according to the second embodiment.
Figure 19B:
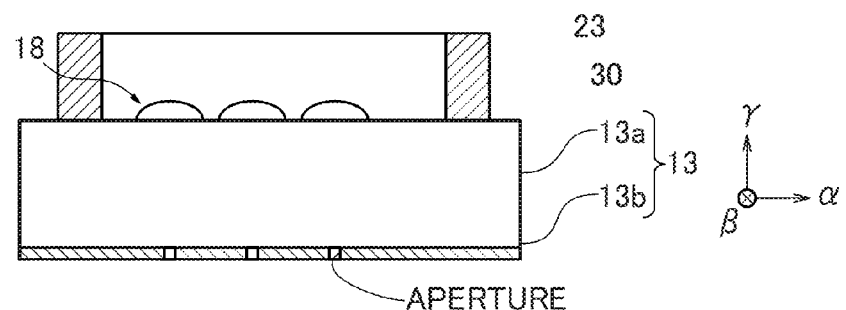
Figure 19C:
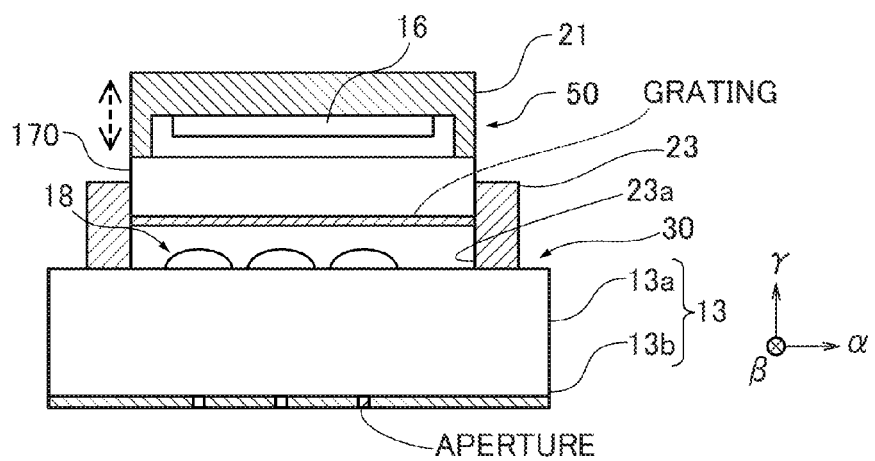

The assembly process of the spectroscopic unit 150 is described referring to FIGS. 19A to 19C.

First, as in the first embodiment, three micro lenses 18a, for example, are attached to the optical element 13 to create a lens unit 30 in FIG. 19A. Then, the bonding element 23 is mounted on the +γ side surface of the lens unit 30 in FIG. 19B.

The linear sensor 16 is then bonded on the inner bottom surface of the package 21 and an aperture end of the package 21 and the +γ side surface of the diffraction element 170 are bonded with an adhesive to create the sensor unit 50. The sensor unit 50 can be assembled before the lens unit 30.

Then, the sensor unit 50 is fitted into the bonding element 23 in FIG. 19C. Alternatively, the bonding element 23 can be placed on the lens unit 30 after the sensor unit 50 is fitted into the bonding element 23. Here, the third and fourth virtual planes are orthogonal to each other.

As in the first embodiment, the sensor unit 50 and lens unit 30 are positioned relative to the γ axis, direction orthogonal to γ axis and therearound while the output signals from the linear sensor 16 are monitored, so that with a light beam from the −γ side of the lens unit 30, the spectroscopic sensors can receive only the +1st order diffracted images.

Specifically, the lens unit 30 and sensor unit 50 are relatively moved along γ axis and in the direction orthogonal to γ axis, and then relatively rotated around the γ axis for position adjustment. The order of adjustment is arbitrarily changeable.

Since the third and fourth virtual planes are orthogonal to each other, the units can be simply positioned in the different directions, as in the first embodiment. As a result, the spectroscopic unit 150 can be easily, quickly assembled.

Further, there is no need for using a spacer to secure a gap between the diffraction element 170 and optical element 13 to place the micro lens array 18 since the diffraction element 170 is fixed on the +Z side surface of the optical element 13 via the bonding element 23.

Also, the diffraction element 170 is bonded on the aperture end of the package 21 containing the linear sensor 16 to create the sensor unit 50. Therefore, the package 21 can be sealed earlier and the linear sensor 16 can be prevented from foreign matter attached on the light receiving surface.

Without a spacer, the number of parts and elements and the number of assembly steps can be reduced from those in the first embodiment, resulting in cost reduction.

The package 21 containing the linear sensor 16 and diffraction element 170 are integrated and the package 21 is sealed. Accordingly, it is possible to prevent foreign matter from attaching on the light receiving surface of the linear sensor 16 and prevent a reduction in the accuracy of spectroscopy.

Further, the diffraction element can be slightly smaller in size than the package, for instance. It can be fitted into the package and the outer side surfaces of the diffraction element can be bonded with the inner side surfaces of the package and the outer side surface of the package can be bonded with the inner side surface of the bonding element. In this case the vertical plane including the bonded surface of the bonding element and sensor unit is orthogonal to the vertical plane including that of the bonding element and lens unit.

Furthermore, the magnitude relations between the bonding element and sensor unit and between the bonding element and lens unit can be reverse. It can be configured that the +Z side surface of the bonding element is bonded with the −Z side surface of the sensor unit, the lens unit is fitted into the bonding element and the inner side surface of the bonding element is bonded with the outer side surface of the sensor unit. In this case the virtual plane including the bonded surface of the bonding element and sensor unit is parallel to XY plane and that including the bonded surface of the bonding element and lens unit is orthogonal to XY plane. Thus, the two virtual planes are orthogonal to each other.

Figure 20:
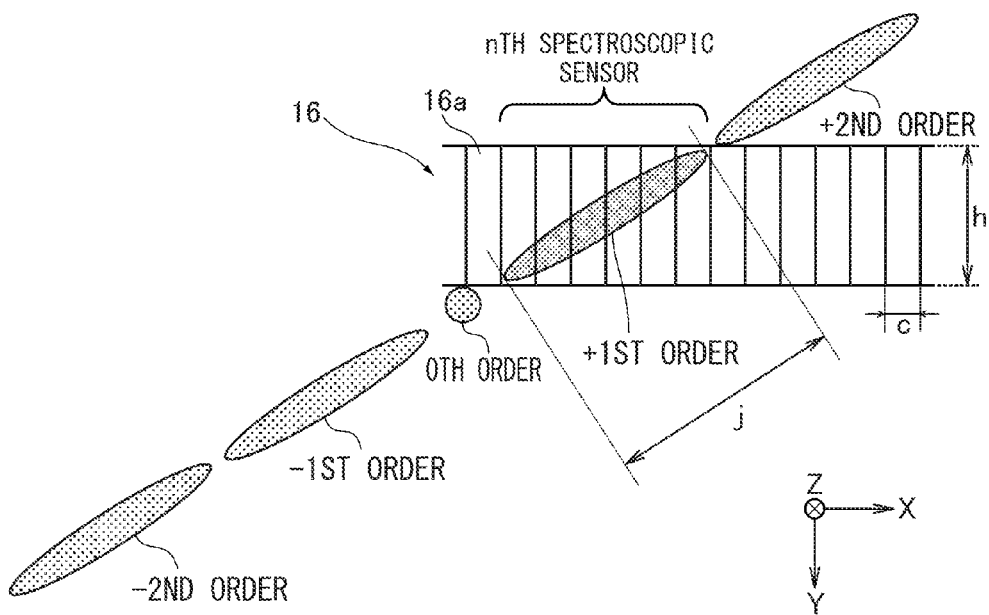
FIG. 20 shows the length j of the diffracted image.

Meanwhile, in general the height h and width c of a pixel (in FIG. 20) are specific to the linear sensor 16. The number of pixels N of a single spectroscopic sensor is determined from the aperture pitch and the magnification of the imaging system 14. The direction of unevenness on the diffraction element is determined so that the inclination angle of the diffracted image on the linear sensor 16 along X axis becomes $\tan^{-1}(h/(N^*c))$.

There is a TDI (time delay integration) linear sensor in which pixel height is adjustable. In this case the pixel height h can be set to an adjusted height.

The necessary number N of bands can be acquired by forming the diffraction element 17 or 170 with the unevenness in the set direction.

The above embodiments use the micro lens array as optical convergent element. Alternatively, it can be a Selfoc® lens array with gradient index lenses.

Further, the bonding element can include a polygonal or elliptic aperture instead of a rectangular one and the package or diffraction element can be formed in shape to be fitted into the aperture of the bonding element. It can be arbitrarily configured as long as the bonding element fitted into the package or diffraction element is relatively moved along Z axis.

For the assembly of the spectroscopic unit, the γ axis can be the other directions than vertical direction.

The structure of the imaging system and that of the light source unit are arbitrarily changeable. The numbers of apertures, micro lens array, and linear sensors are arbitrarily changeable.

Further, the present embodiment describes an example where the image forming device is of electrophotographic type. Alternatively, it can be of inkjet type. In this case it can correct a color variation in a single paper or over papers by adjusting an ink blow amount in accordance with a head position or adjusting dot patterns.

Further, the number of toner colors can be five or six instead of four, for example.

In the present embodiment the toner image is transferred from the photoreceptor drums via the transfer belt. Alternatively, the toner image can be directly transferred on a paper.

The image forming device can use a medium such as photographic papers to produce colors by the thermal energy of beam spots.

Figure 21:
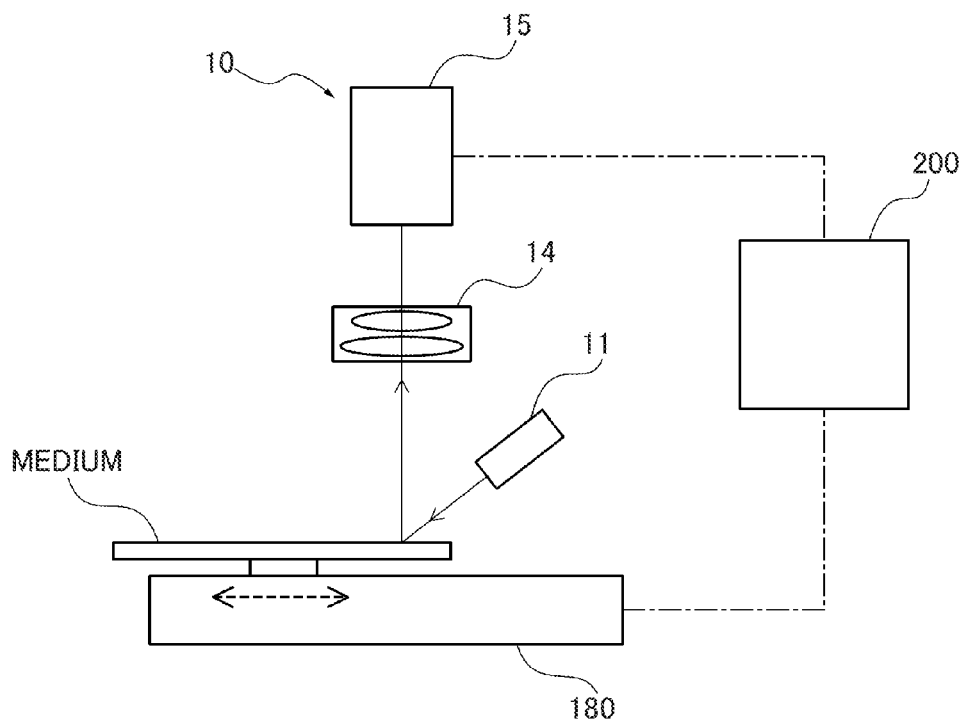
FIG. 21 shows an example of the structure of an image evaluating unit by way of example.

Further, the spectrometer 10 is applicable to other devices in addition to the image forming device, for example, to an image evaluating unit to evaluate image quality on a medium, as shown in FIG. 21. The image evaluating unit comprises the spectrometer 10, a moving system 180 to move at least one of the medium and the spectrometer 10 and a processor 200 to evaluate an image according to the output signal of the light receiving element (as linear sensor) of the spectroscopic unit 15. This image evaluating unit can properly evaluate image quality and is adoptable for an evaluation device for determining authenticity or kinds of paper money or credit cards. Also, it can evaluate images printed on materials such as plastic in addition to paper.

For a target object such as a sheet of paper with plasticity, the moving system can include a rotary drum of which a sheet is attached on the surface to rotate around the axis.

Although the present invention has been described in terms of exemplary embodiments, it is not limited thereto. It should be appreciated that variations or modifications may be made in the embodiments described by persons skilled in the art without departing from the scope of the present invention as defined by the following claims.

What is claimed is:

1. A spectrometer comprising:
a light source to project a light beam to a target object;
a spectral element which includes an optical element to disperse the light beam reflected by the target object and including a diffraction element to diffract the light beam;
a light receiving element to receive, at pixels, light beams with different spectral characteristics from each other dispersed by the spectral element, wherein the diffraction element and the light receiving element are integrally formed,
a sub unit in which the optical element and the diffraction element are fixed in a certain relative position;
a holder to hold the light receiving element; and
a bonding element to bond the sub unit and the holder, wherein
a virtual plane including a surface of the bonding element on which the sub unit is bonded and a virtual plane including a surface of the bonding element on which the holder is bonded are orthogonal to each other.

2. A spectrometer according to claim 1, wherein:
the spectral element includes an optical element with an aperture through which the light beam reflected by the target object transmits, and an imaging element to image the light beam having transmitted through the optical element; and
the diffraction element, optical element, and imaging element are integrally formed.

3. A spectrometer according to claim 2, wherein
a sub unit in which the diffraction element and the light receiving element are fixed in a certain relative position; and
a bonding element to bond the sub unit and the optical element, wherein
a virtual plane including a surface of the bonding element on which the optical element is bonded and a virtual plane including a surface of the bonding element on which the sub unit is bonded are orthogonal to each other.

4. A spectrometer according to claim 2, wherein the imaging element is attached in the optical element.

5. An image evaluating unit to evaluate a quality of an image on a medium, comprising:
a spectrometer according to claim 2, to perform a spectroscopy on an image;
a moving system to move at least one of the medium and the spectrometer; and
a control system to control the moving system.

6. An image forming device comprising:
a photoreceptor on which an image is formed;
a spectrometer according to claim 2; and
a processor to relatively move the spectrometer and the photoreceptor and acquire a spectral characteristic of the image formed on the photoreceptor on the basis of an output of the spectrometer.

7. A spectrometer according to claim 1, wherein
the light source includes a light source with a blue LED to project a white light beam.

8. An image evaluating unit to evaluate a quality of an image on a medium, comprising:
a spectrometer according to claim 1, to perform a spectroscopy on an image;
a moving system to move at least one of the medium and the spectrometer; and
a control system to control the moving system.

9. An image forming device comprising:
a photoreceptor on which an image is formed;
a spectrometer according to claim 1; and
a processor to relatively move the spectrometer and the photoreceptor and acquire a spectral characteristic of the image formed on the photoreceptor on the basis of an output of the spectrometer.

* * * * *